United States Patent
Gan

(10) Patent No.: US 8,202,948 B2
(45) Date of Patent: *Jun. 19, 2012

(54) PHOSPHORUS-CONTAINING COMPOUNDS USEFUL FOR MAKING HALOGEN-FREE IGNITION-RESISTANT POLYMERS

(75) Inventor: Joseph Gan, Strasbourg (FR)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/939,725

(22) Filed: Nov. 4, 2010

(65) Prior Publication Data

US 2011/0054078 A1 Mar. 3, 2011

Related U.S. Application Data

(62) Division of application No. 11/587,119, filed on Oct. 20, 2006, now abandoned.

(60) Provisional application No. 60/575,602, filed on May 28, 2004.

(51) Int. Cl.
C08G 14/12 (2006.01)
C08L 63/00 (2006.01)
C08L 63/04 (2006.01)

(52) U.S. Cl. ...... 525/481; 525/92 D; 525/109; 525/118; 525/119; 525/120; 525/122; 525/390; 525/437; 525/461; 525/465; 528/158

(58) Field of Classification Search .................. None
See application file for complete search history.

(56) References Cited

U.S. PATENT DOCUMENTS

| | | |
|---|---|---|
| 2,409,910 A | 10/1946 | Stober |
| 2,515,250 A | 7/1950 | McIntire |
| 2,669,751 A | 2/1954 | McCurdy et al. |
| 2,727,884 A | 12/1955 | McDonald et al. |
| 2,846,408 A | 8/1958 | Brochhagen et al. |
| 2,848,428 A | 8/1958 | Rubens |
| 2,928,130 A | 3/1960 | Gray |
| 3,121,130 A | 2/1964 | Wiley et al. |
| 3,121,911 A | 2/1964 | Lightner |
| 3,123,655 A | 3/1964 | Otting et al. |
| 3,257,357 A | 6/1966 | Stamatoff |
| 3,257,358 A | 6/1966 | Stamatoff |
| 3,305,528 A | 2/1967 | Wynstra |
| 3,306,874 A | 2/1967 | Hay |
| 3,306,875 A | 2/1967 | Hay |
| 3,346,520 A | 10/1967 | Lee |
| 3,639,522 A | 2/1972 | Narayana et al. |
| 3,770,688 A | 11/1973 | Hamann et al. |
| 3,815,674 A | 6/1974 | Best et al. |
| 3,960,792 A | 6/1976 | Nakamura |
| 3,966,381 A | 6/1976 | Suh |
| 4,066,628 A | 1/1978 | Ashida et al. |
| 4,085,073 A | 4/1978 | Suh et al. |
| 4,146,563 A | 3/1979 | Ratafia et al. |
| 4,157,324 A | 6/1979 | Culbertson |
| 4,229,396 A | 10/1980 | Suh et al. |
| 4,302,910 A | 12/1981 | Tschacher |
| 4,409,369 A | 10/1983 | Lyons et al. |
| 4,421,866 A | 12/1983 | Suh et al. |
| 4,438,224 A | 3/1984 | Suh et al. |
| 4,454,086 A | 6/1984 | Corbett et al. |
| 4,486,550 A | 12/1984 | Rhoads |
| 4,572,819 A | 2/1986 | Priddy et al. |
| 4,585,825 A | 4/1986 | Wesselmann |
| 4,666,987 A | 5/1987 | Burmester et al. |
| 4,863,979 A | 5/1987 | Beyersdorf et al. |
| 4,925,901 A | 5/1990 | Bertram et al. |
| 4,963,399 A | 10/1990 | Gill |
| 5,066,735 A | 11/1991 | Walker et al. |
| 5,112,932 A | 5/1992 | Koenig et al. |
| 5,157,080 A | 10/1992 | Gardner et al. |
| 5,275,853 A | 1/1994 | Silvis et al. |
| 5,308,895 A | 5/1994 | Gan et al. |
| 5,314,720 A | 5/1994 | Gan et al. |
| 5,496,910 A | 3/1996 | Mang et al. |
| 6,180,695 B1 * | 1/2001 | Ito et al. ................. 523/451 |
| 6,201,101 B1 | 3/2001 | Tozzola et al. |
| 6,545,631 B2 | 4/2003 | Hudson et al. |
| 6,639,372 B2 | 10/2003 | Gotou |
| 6,645,631 B2 | 11/2003 | Gan et al. |

FOREIGN PATENT DOCUMENTS

| | | |
|---|---|---|
| DE | 4308184 | 3/1991 |
| DE | 4308185 | 3/1993 |
| DE | 4308187 | 3/1993 |
| EP | 0384939 | 3/1989 |
| EP | 0384940 | 3/1989 |
| EP | 549120 | 11/1992 |
| EP | 526488 | 11/1994 |
| EP | 806429 | 11/1997 |

(Continued)

OTHER PUBLICATIONS

Catalog of Chemical Suppliers, methanephosphonic acid, 2011, one page.*

(Continued)

*Primary Examiner* — Robert Sellers

(57) ABSTRACT

Phosphorus-containing compounds are disclosed which are obtainable by reacting:
(A) at least one organophosphorus compound having a group selected from the group H—P=O; the group P—H and the group P—OH; and
(B) at least one compound having the following Formula (I):

$$[R'(Y)_{m'}]_m(X\text{—}O\text{—}R'')_n \qquad \text{Formula (I)}$$

wherein
R' is an organic group;
Y is a functional group selected from the group consisting of hydroxy, carboxylic acid, and amine;
X is a hydrocarbylene group;
R'' is hydrogen or a hydrocarbyl group having from 1 to 8 carbon atoms, R is alkyl or aryl group having from 1 to 12 carbon atoms;
m', m and n are, independently, numbers equal to or greater than 1; and
(C) a thermosetting or thermoplastic composition.

13 Claims, No Drawings

FOREIGN PATENT DOCUMENTS

| | | |
|---|---|---|
| EP | 0408990 | 11/1998 |
| EP | 787161 | 6/2001 |
| EP | 0458502 | 6/2003 |
| JP | 2002-53633 A * | 2/2002 |
| WO | WO 96/07685 | 3/1996 |
| WO | WO 98/31750 | 7/1998 |
| WO | WO 99/00451 | 1/1999 |
| WO | WO 99/00451 A1 * | 1/1999 |
| WO | WO 00/27921 | 5/2000 |

OTHER PUBLICATIONS

U.S. Appl. No. 10/456,127, filed Dec. 9, 2004, The Dow Chemical Company.

* cited by examiner

PHOSPHORUS-CONTAINING COMPOUNDS USEFUL FOR MAKING HALOGEN-FREE IGNITION-RESISTANT POLYMERS

CROSS-REFERENCE TO RELATED APPLICATIONS

This application is a Division of application Ser. No. 11/587,119 filed on Oct. 20, 2006. Application Ser. No. 11/587,119 claims the benefit of U.S. Provisional Application 60/575,602 filed on May 28, 2004.

The present invention is in the field of phosphorus-containing compounds; their use as flame retardants for polymers, especially for epoxy, polyurethane, thermosetting resins and thermoplastic polymers; and the use of such flame retardant-containing polymers to make protective coating formulations and ignition-resistant fabricated articles, such as electrical laminates, polyurethane foams, and various molded and/or foamed thermoplastic products.

Ignition-resistant polymers have typically utilized halogen-containing compounds to provide ignition resistance. However, there has been an increasing demand for halogen-free compositions in ignition-resistant polymers markets. Proposals have been made to use phosphorus-based flame retardants instead of halogenated fire retardants in thermoset epoxy resin formulations as described in, for example, EP A 0384939, EP A 0384940, EP A 0408990, DE A 4308184, DE A 4308185, DE A 4308187, WO A 96/07685, and WO A 96/07686.

However, further improvements in flame resistance are desired. There is also a desire to improve the manufacture and performance of the ignition-resistant polymer composition.

Therefore, there remains a need to provide a halogen-free polymer composition having good ignition-resistance and heat resistance; and which overcomes the disadvantages of prior art compositions which exhibit poor properties such as poor moisture resistance and low Tg.

One aspect of the present invention is directed to a process for making a phosphorus-containing compound comprising reacting:
(A) at least one organophosphorus compound having a group selected from the group H—P═O; the group P—H and the group P—OH with
(B) at least one compound having the following Formula (I):

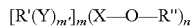   Formula (I)

wherein
R' is an organic group;
Y is a functional group selected from the group consisting of hydroxy, carboxylic acid, and amine;
X is a hydrocarbylene group;
R" is hydrogen or a hydrocarbyl group having from 1 to 8 carbon atoms;
R is alkyl or aryl group having from 1 to 12 carbon atoms; and
m', m and n are, independently, numbers equal to or greater than 1.

Another aspect of this invention is directed to phosphorus-containing compounds obtainable according to the above process (herein referred to as "Compound (I)"), particularly phosphorus-containing compounds comprising the reaction product of:
(A) at least one organophosphorus compound having a group selected from the group H—P═O, the group P—H and the group P—OH; and
(B) at least one compound having the following Formula (I):

   Formula (I)

wherein
R' is an organic group;
Y is a functional group selected from the group consisting of hydroxy, carboxylic acid, and amine;
X is a hydrocarbylene group;
R" is hydrogen or a hydrocarbyl group having from 1 to 8 carbon atoms, R is alkyl or aryl group having from 1 to 12 carbon atoms; and
m', m and n are, independently, numbers equal to or greater than 1.

More particularly, the phosphorus containing compounds are those having at least two phenolic aromatic rings preferably linked by a hydrocarbylene group or hydrocarbylene ether group and a phosphorus content of at least 4 wt-percent.

Other aspects of the present invention include for example compounds, compositions and/or formulations obtainable by reacting, blending or mixing Compound (I) with other components such as a thermosetting resin or a thermoplastic material or a mixture of a thermosetting resin and a thermoplastic material to form various ignition resistant compounds, compositions or formulations useful in various applications such as prepregs, laminates, coatings, molding articles and composite products.

For example, one aspect of the present invention is directed to phosphorous-containing epoxy compounds obtainable by reacting at least one of the above phosphorus-containing compounds (Compound (I)) with at least one compound having one epoxy group per molecule, for example, epichlorohydrin, glycidylether of polyphenols (such as bisphenol A, Bisphenol F, phenol novolac, cresol phenol novolac), glycidylether of methacrylate, glycidylether of acrylate and other similar compounds. Such phosphorus-containing epoxy compounds may also be combined with at least one curing agent, and optionally at least one crosslinkable epoxy resin other than the phosphorus-containing epoxy compound, to obtain curable ignition-resistant epoxy resin compositions. Such epoxy resin compounds and phosphorus-containing epoxy compounds may be used to make prepregs, which may be used to make laminates and circuit boards useful in the electronics industry. The epoxy compounds may also be used to coat metallic foils such as copper foils to make resin coated copper foils for a so call build up technology.

Another aspect of the present invention is directed to phosphorous-containing epoxy resin curable formulations comprising (i) Compound (I), (ii) an epoxy resin or a mixture of epoxy resins, (iii) optionally, a co-crosslinker, (iv) optionally, a catalyst, and (v) optionally, a Lewis acid.

A further aspect of this invention is directed to benzoxazine group-containing compounds obtainable by reacting (i) at least one of the above phosphorus-containing compounds (Compound (I)) having a phenolic functionality or an amine functionality with either (ii) a primary amine and a formaldehyde or (iii) a hydroxyl-containing compound and a formaldehyde to form a phosphorus-containing benzoxazine compound. Also useful in the present invention are benzoxazine compounds that form a polybenzoxazine upon heating.

Yet another aspect of the present invention is directed to curable flame-resistant epoxy resin compositions comprising (i) the above phosphorus-containing benzoxazine-containing compound, (ii) a crosslinkable epoxy resin or a blend of two or more epoxy resins having more than one epoxy group per molecule, (iii) optionally a curing agent and, (ii) optionally, a curing catalyst to obtain a curable flame resistant epoxy resin composition. Such curable flame resistant epoxy resin compositions may be used to make prepregs, which may be used to make laminates and circuit boards useful in the electronics industry. The epoxy resin composition may also be used to coat metallic foils such as copper foils to make resin coated copper foils for a so call build up technology.

Another aspect of the present invention is directed to the thermolabile group-containing phosphorus-containing compounds obtainable by reacting (i) at least one of the above phosphorus-containing compounds, Compound (I), having a phenolic functionality with (ii) a thermolabile group-containing compound such as a compound having t-butyloxycarbonyl groups to form a modified phosphorus-containing compound. The modified phosphorus-containing compounds are stable at ambient temperature and its thermolabile groups degrade at elevated temperature leading to gas generation. These modified phosphorus-containing compounds can be blended with different thermosetting systems to generate gas bubbles leading to encapsulation of gas in the crosslinked systems having lower dielectric constant and loss factor or products having lower weight when the processing temperature is well controlled.

Yet another aspect of this invention is directed to polyols obtainable by reacting (i) at least one of the above phosphorus-containing compounds, Compound (I), with an (ii) ethoxy and/or a propoxy group. Such polyols are useful intermediates for making ignition-resistant polyurethane resins.

The phosphorus-containing compounds, Compounds (I), according to this invention, and derivatives thereof, may also be combined with at least one thermoplastic resin to make an ignition-resistant thermoplastic composition.

The phosphorus-containing compounds, Compounds (I), according to this invention, and derivatives thereof, may also be combined with at least one thermoplastic resin and thermosetting systems (epoxy and curing agents) to make an ignition-resistant thermoplastic containing thermosetting compositions.

Other aspects of the present invention are evident from the detailed description and claims which follow.

DEFINITIONS

The terms "organo" and "organic" as used herein refer to compounds or moieties comprising carbon atoms and hydrogen atoms, and optionally hetero atoms (that is, atoms which are not carbon or hydrogen), which are primarily covalently bonded to one another. Preferred optional hetero atoms include oxygen atoms and nitrogen atoms. The number of hetero atoms in the "organo" and "organic" compounds and moieties is less than the number of carbon atoms, and is preferably less than half the number of carbon atoms.

The terms "hydrocarbyl" and "hydrocarbylene" refer to chemical structures or moieties comprising carbon atoms and hydrogen atoms covalently bonded to each other. Such structures or moieties may contain atoms other than, and in addition to, carbon and hydrogen (referred to herein as "hetero" atoms) insofar that the hetero atoms do not add significant reactive functionality to such moieties. An example of such acceptable hetero atoms are ether oxygen atoms. Such moieties preferably do not contain any hetero atoms.

The expression "substantially free", as that expression is used herein when used with reference to a particular substance, means that a starting material or product generally contains less than 10 weight percent, preferably less than 5 weight percent, more preferably less than 1 weight percent, and more preferably zero weight percent, of a particular substance.

The expression "wt. percent" means "weight-percent".

Phosphorus-Containing Compound, Compound (I)

The phosphorous-containing compound of the present invention, herein referred to as Compound (I), is obtainable from the reaction between the organophosphorus compound, herein referred to as Component (A), and the compound of Formula (I), herein referred to as Component (B). One of the advantages of Compound (I) is that it contains a phosphorus element in its chemical structure making it useful as a raw material for preparing flame resistant materials. Another advantage of Compound (I) is that it has an active hydrogen group making it useful as a reactive starting material for reacting with other polymers. For example, Compound (I) may contain active hydrogen groups such as hydroxyl groups which makes it reactive with epoxy resins. In this embodiment, Compound (I) can be considered as a crosslinking agent, curing agent or hardener for an epoxy resin.

Compound (I) generally has a phosphorous content of at least 4 wt-percent and preferably at least 6 weight-percent make it useful as a flame retardant material. Compound (I) is preferably substantially free of bromine atoms, and more preferably substantially free of halogen atoms. Compound (I) may also be used as a non-reactive additive, such as when used with a thermoplastic or other thermosetting systems. For example, Compound (I) can be used a charring agent to provide an insulating layer of char at elevated temperatures for thermoplastic formulations and for thermosetting formulations.

Compounds Corresponding to Formula (I), Component (B)

Compounds which fall within the scope of Formula (I) as described above are also referred herein as Component (B).

In Formula (I), each (—X—O—R") group may be bonded to the same or different atom in "R'". Preferably, each (—X—O—R") group is bonded to a different atom in "R'".

"X" preferably has from 1 to 8, and more preferably from 1 to 4, carbon atoms. In a preferred embodiment, "X" is an alkylene group having from 1 to 8, preferably from 1 to 4, and even more preferably 1 or 2, carbon atoms, such as methylene, ethylene, propylene, isopropylene, butylene, isobutylene. Methylene is the most preferred "X" group.

"R''" may be a hydrogen atom or a hydrocarbyl group having 1, preferably at least 2, and more preferably at least 3, carbon atoms; and preferably up to 20, more preferably up to 12, and up to 6, and even more preferably up to 5, carbon atoms. The hydrocarbyl group is preferably an alkylene group, such as methyl, ethyl, propyl, isopropyl, butyl, isobutyl, pentyl, hexyl, heptyl, and octyl. Most preferred for the R" group are methyl, butyl and isobutyl.

"R'" preferably comprises at least one arylene group and optionally at least one hydrocarbylene group or hydrocarbylene ether group. The "R'" group more preferably comprises at least two aromatic groups linked to each other by a hydrocarbylene group or hydrocarbylene ether group. The aromatic groups are preferably phenyl groups and the hydrocarbylene group is preferably "X" as defined above, most preferably a methylene group and the hydrocarbylene ether is preferably a methylene oxy group.

"Y" is a functional group capable of reacting with an epoxy group, an ethoxy group or a propoxy group. The "Y" functional groups are preferably selected from hydroxyl (—OH), carboxylic acid (—C(O)OH), carboxylate (—C(O)OR'"), carboxylic acid anhydride, a primary or a secondary amine (—NH$_2$, —NHR"" or =NH, wherein "=" refers to two covalent bonds to the same or different atoms of "R'"), —SH$_5$, —SO$_5$H, —CONH$_2$—NHCOOR, and phosphinates (HO—P[R"]$_2$=O), or phosphites (H—P[OR"]$_2$=O).

"R'''''" may be an alkali metal, such as Na⁺ or K⁺, or a hydrocarbyl group having up to 8, preferably up to 4, and more preferably up to 2, carbon atoms, such as methyl, ethyl, propyl, isopropyl, butyl, isobutyl.

"R''''" is hydrogen or a hydrocarbyl group, such as an aryl group, an alkyl group, or an alkaryl group, which preferably has up to 20, more preferably up to 12, and even more preferably up to 4, carbon atoms.

The carboxylic acid anhydride is preferably selected from substituted or unsubstituted succinic anhydride, maleic anhydride and phthalic anhydride. Each substituent, when present is one or more hydrogen atoms or hydrocarbyl group, such as an alkyl group preferably having up to 12, and more preferably, up to 4, carbon atoms.

The hydroxyl, carboxylic acid and carboxylic acid anhydride functionalities are preferred, and the hydroxyl functionality is most preferred for the R'''' group.

The preferred compounds of Formula (I) are those compounds that meet the Formula (I), [R'(Y)$_m$]$_m$(X—O—R'')$_n$, and at least one (X—O—R'') group is in the middle of the backbone of the chemical structure. For example, preferred compounds include those that contain at least two (X—O—R'') groups on at least one of the same R'(Y)$_{m'}$ groups. In addition, the compounds that are useful in the present invention include, for example, those that meet the following criteria:

(a) n is preferably greater than m; or
(b) when n is equal 1, then m must be greater than 3 and at least one (X—O—R'') group is in the middle of the backbone of the chemical structure; or
(c) when m is equal to 1, then n must be greater than 1; or
(d) when n is equal to 2, then at least one of the (X—O—R'') groups must be in the middle of the backbone of the chemical structure.

In Formula (I), m' is preferably less than 10, m is preferably less than 100, and n is preferably less than 200.

Preferred compounds of Formula (I) may be represented by the following Formula (II):

$$[Ar(Y)_{m'}—X']_a[Ar(Y)_{m'}—X]_b(X—O—R'')_n \quad \text{Formula (II)}$$

wherein each "Ar" independently is an aromatic group, preferably a phenyl group, optionally substituted with one or more groups, preferably selected from alkyl, alkoxy, and alkanol, having 1 to 4 carbon atoms (for example, methyl, methoxy, methanol, ethyl, ethoxy, ethanol, propyl, propoxy, propanol, isopropyl, isopropanol, butyl, butoxy, butanol) such as, for example, a tolylene and/or xylene group; at least one of the (X—O—R'') groups is on at least one of the Ar groups; "n", "m'", "X", "Y", and "R''" have the same meaning as in Formula (I); "X'" each independently may be X, X—O—X, or X—O—X—O—X; "a" and "b" each independently represent a number equal to or greater than zero, but both cannot be zero.

In Formula (II), "a" is preferably up to 100, "b" is up to 100 and "n" is preferably up to 200.

A more preferred compound of Formula (I) may be represented by the following Formula (III):

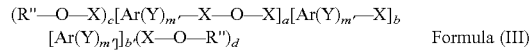

Formula (III) wherein "Ar", "m'", "a", "b", "X", "Y", and "R''" have the same meaning as in Formula (II); subscripts "b", "c" and "d" each independently represent a number equal to or greater than zero. In Formula (III), "c" is preferably up to 200 and "d" is preferably up to 200.

The "Y" groups are preferably bonded directly to an Ar group. Examples of preferred "Ar(Y)" include phenol, cresol, and xylenol, and the corresponding divalent counterparts thereof.

The (X—O—R'') group in each unit with the subscripts "c" and "d" having a value greater than zero is bonded directly to a member of an "Ar" group of another unit in Formula (III), which has the same or different unit formula.

The units with the subscripts "a", "b", and "b" may be present in any order in a random or block configuration. Each of subscripts "a", "b", "b", "c" and "d" independently are preferably at least 1. Each of subscripts "a", "b", "b", "c" and "d" independently are preferably zero, more preferably at least 1, and even more preferably at least 5; yet more preferably at least 10 and preferably not greater than 1000, and more preferably not greater than 100. In one embodiment, the subscripts "a", "b", "b", "c" and "d" independently are preferably not greater than 50, more preferably not greater than 30, and even more preferably not greater than 10.

Preferred compounds of Formula (I) may further be represented by the following Formula (IV):

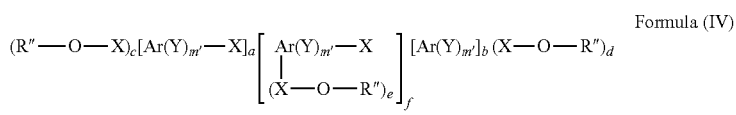

Formula (IV)

wherein "e" is an integer from 0 to 4; "f" is 1 or greater and preferably less than 50; and m', R'', Ar, Y, X, "a", "b", "c" and "d" are as defined above with reference to Formula (III).

Preferred compounds of Formula (III) may be represented by the following formulas, Formula (V) and Formula (VI);

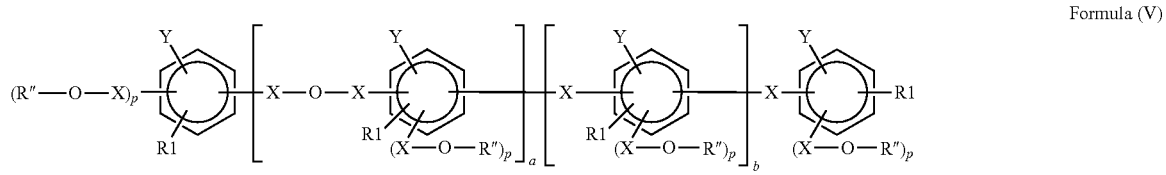

Formula (V)

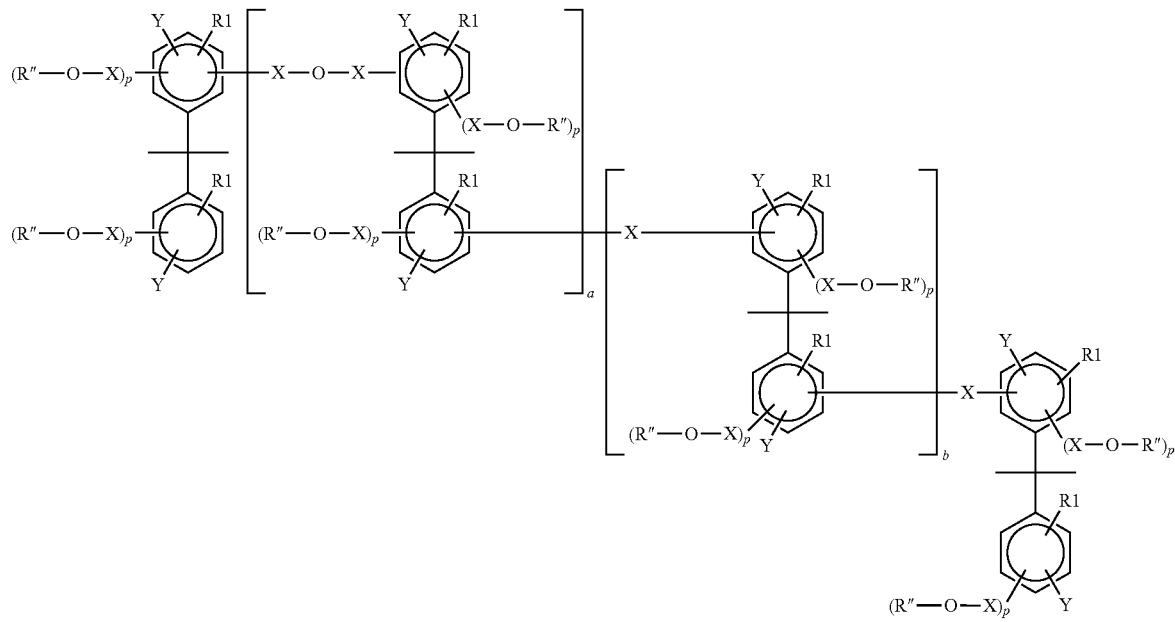

Formula (VI)

wherein "R1" each independently is hydrogen or an alkyl group having from 1 to 10 carbon atoms, "p" each independently represents a number from zero to 4;

"a" and "b" each independently represent a number equal to or greater than zero;

and "X", "Y" and "R" have the same meaning as in Formula (III).

In a preferred embodiment, the compounds of Formula (III), that is Component (B), may be prepared by first reacting (a) phenols, cresols, xylenols, biphenol-A, and/or other alkyl phenols and (b) formaldehyde, to form one or more monomeric, dimeric or higher condensation products. Subsequently, the condensation products resulting from reacting (a) and (b) above are modified by etherification, either partially or fully etherified, with at least one monomeric alcohol. The monomeric alcohol is ROH wherein R is the same as defined above for Formula (I). Examples of the resultant etherified products which can be used as Component (B), are for example etherified resole resins such as those described in U.S. Pat. No. 4,157,324, and U.S. Pat. No. 5,157,080.

Component (B) made by the above reaction of (a) and (b) preferably contains low amounts of the starting raw materials such phenol, cresol, bisphenol A and formaldehyde as residual monomers in the reaction product (that is Component (B)) for example less than 3 wt percent, preferably less than 2 wt percent and more preferably less than 1 wt percent.

It is preferable to use etherified resoles over non-etherified resoles as Component (B) in the present invention because etherified resoles are more storage stable at room temperature (about 25° C.) whereas non-etherified resoles have a tendency to undergo self condensation; and at elevated temperature, typically greater than 25° C., preferably greater 100° C. and more preferably greater 150° C. and even more preferably greater than 170° C., and generally less than 250° C. and preferably less than 220° C. resoles have tendency to undergo self condensation rather than to react with the phosporous compounds of Component (A). Thus, for the present invention, it is advantageous to select etherified resoles as Component (B) that have a lower tendency to undergo self condensation and that tend to favor the main condensation reaction with Component (A) for example via the alkyl group R".

An example of the preferred condensation product prepared by reacting (a) and (b) as described above is illustrated as according the following general chemical equation:

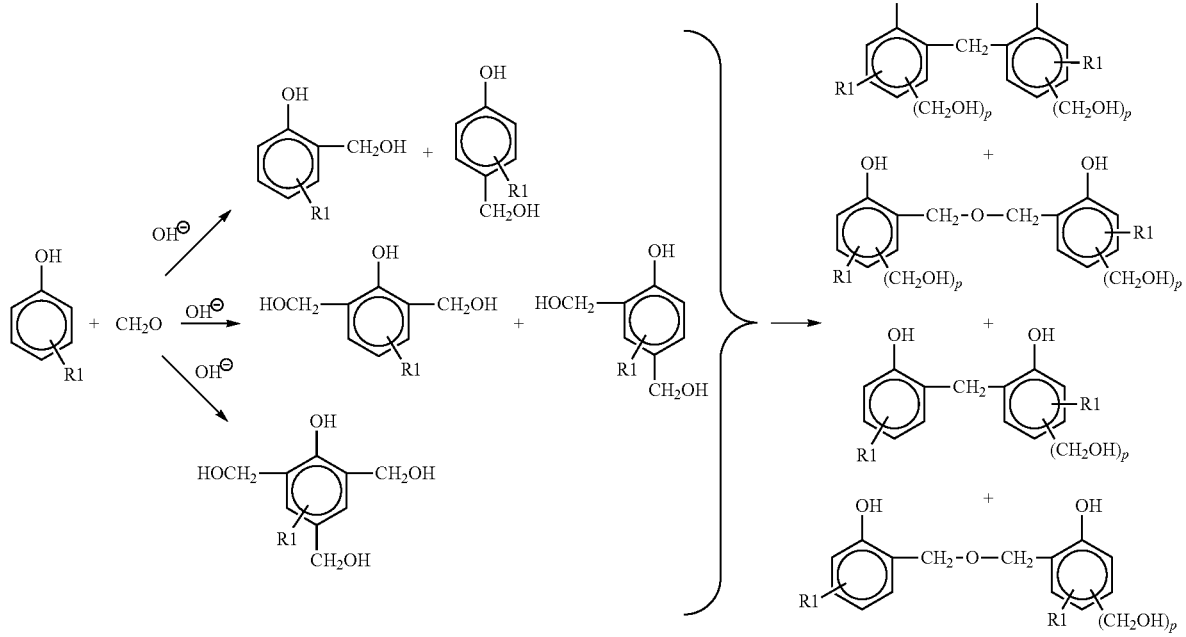

wherein "p" is an integer from 1 to 4 independently; and "R1" is hydrogen or an alkyl group having from 1 to 10 carbon atoms independently.

The above reaction provides a mixture of different isomer condensation products having methylene linkage or a dimethylene ether linkage such as (1) having two $CH_2OH$ (one on each benzene ring; or (2) having one $CH_2OH$ group on one benzene ring.

The $CH_2OH$ groups in the above condensation products illustrated in the above general chemical equation are partially or fully etherified with an alcohol to provide Component (B) useful in the present invention. In this embodiment a mixture of different isomers of the condensation product can be formed.

The number average molecular weight of the compounds of Formulas (I) to (IV) is preferably at least 50, more preferably at least 200, and even more preferably at least 500; and is preferably not greater than 10,000, more preferably not greater than 8,000, and even more preferably not greater than 5000. The weight average molecular weight is preferably at least 100, more preferably at least 400, and even more preferably 1000; and is preferably not greater than 15,000, more preferably not greater than 3,000, and even more preferably not greater than 1,500.

Component (B) is preferably substantially free of bromine atoms, and more preferably substantially free of halogen atoms.

An example of Component (B) is shown in the following chemical Formula (VII):

Formula (VII)

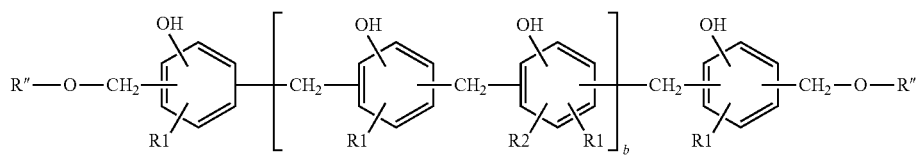

wherein "R2" each independently is hydrogen, an alkyl group having from 1 to 10 carbon atoms, $CH_2OH$, or $CH_2OR'''$;
"R1" each independently is hydrogen or an alkyl group having from 1 to 10 carbon atoms;
"R'''" is a hydrogen or a hydrocarbyl group having from 1 to 8 carbon atoms; and
"b" represents a number equal to or greater than zero.

Other examples of Component (B) are shown in the following chemical formulas, Formula (VIII) and Formula (VIIIa):

Formula (VIII)

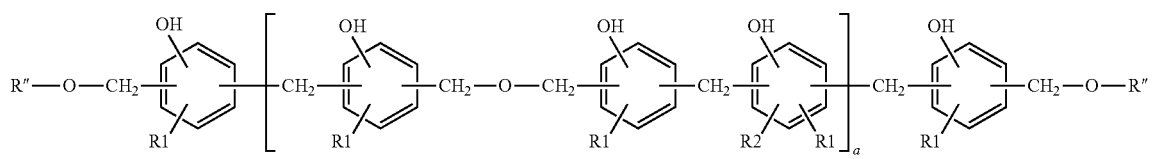

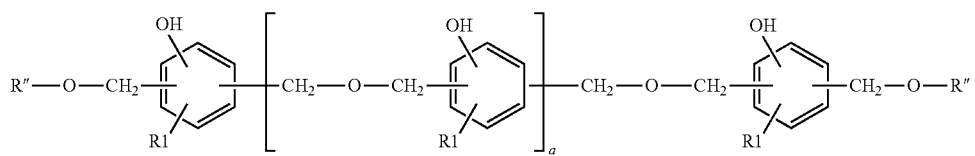

Formula (VIIIa)

wherein "R2" each independently is hydrogen, an alkyl group having from 1 to 10 carbon atoms, $CH_2OH$, or $CH_2OR''$;

"R1" each independently is hydrogen or an alkyl group having from 1 to 10 carbon atoms;

"R''" is a hydrogen or a hydrocarbyl group having from 1 to 8 carbon atoms; and

"a" represents a number equal to or greater than zero.

Still other examples of Component (B) are shown in the following chemical formulas Formula (IX) and Formula (IXa):

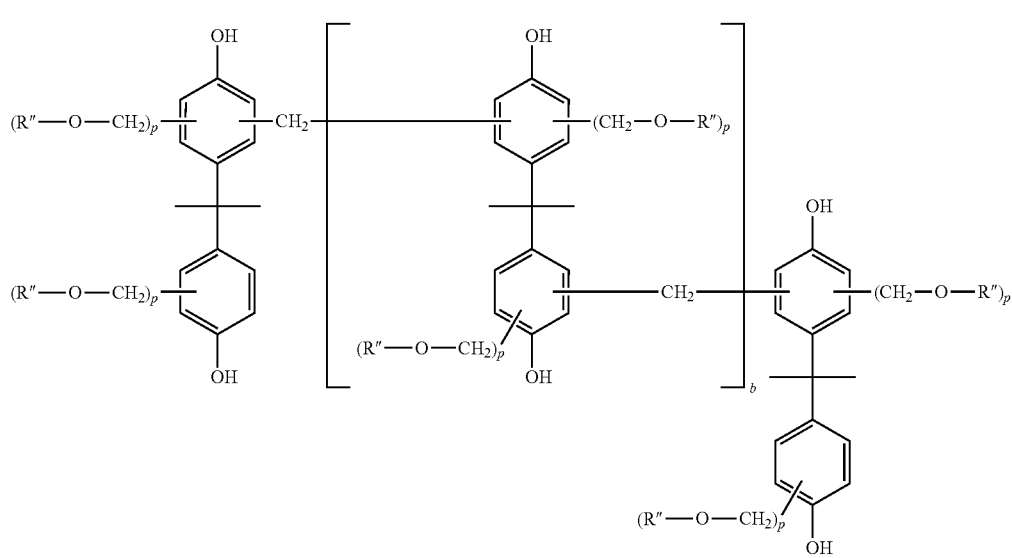

Formula (IX)

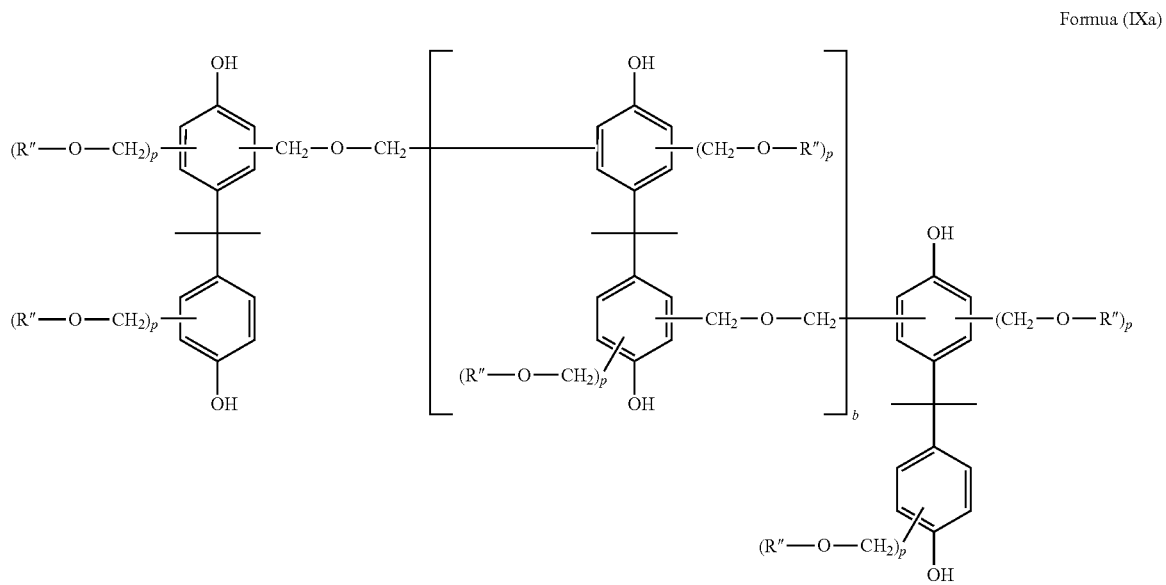

Formua (IXa)

wherein "R'''" is a hydrogen or a hydrocarbyl group having from 1 to 8 carbon atoms; "b" represents a number equal to or greater than zero; and
"p" represents a number equal to or greater than zero.

Examples of commercially available products suitable for use as Component (B) include SANTOLINK™ EP 560, which is a butyl etherified phenol formaldehyde condensation product and PHENODUR™ VPR 1785/50, which is a butoxymethylated phenol novolac which the manufacturer characterizes as a highly butyl etherified resole based on a cresol mixture with a weight average molecular weight from 4000 to 6000 and a polydispersity from 2 to 3. Both of these products are available from UCB Group, a company headquartered in Brussels, Belgium, and its affiliate, UCB GmbH & Co. KG, a company incorporated in Germany. Other resole compounds available from UCB include for example PHENODUR PR 401, PHENODUR PR 411, PHENODUR PR 515, PHENODUR PR 711, PHENODUR PR 612, PHENODUR PR 722, PHENODUR PR 733, PHENODUR PR 565, and PHENODUR VPR 1775.

Other resole compounds available from Bakelite include for example BAKELITE PF 0751 LA, BAKELITE PF 9075 DF, BAKELITE 9900LB, BAKELITE 9435 LA, BAKELITE 0746 LA, BAKELITE 0747 LA, BAKELITE 9858 LG, BAKELITE 9640 LG, BAKELITE 9098LB, BAKELITE 9241 LG, BAKELITE 9989 LB, BAKELITE 0715 LG, BAKELITE 7616 LB, and BAKELITE 7576 LB.

Organophosphorus-Containing Compounds, Component (A)

The organophosphorus-containing compound, Component (A), may be selected from compounds having a group selected from H—P=O, P—H, and P—OH each single "—" of the groups or each "—" of "=" referring to a bond between the phosphorus atom "P" and an organic moiety. The phosphorus atom may be bonded to two separate organic moieties or may be bonded to one organic moiety. When bonded to one organic moiety, the bonds may connect with the same atom of the organic moiety to form a double bond or, preferably, may be single bonds connecting the phosphorus atom with different atoms in the same organic moiety.

The organophosphorus-containing compound preferably corresponds to the following Formulas (X) through (XXII):

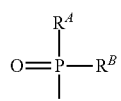  Formula (X)

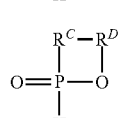  Formual (XI)

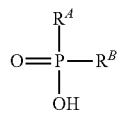  Formula (XII)

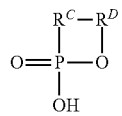  Formula (XIII)

 $R^A PH_2$  Formula (XIV)

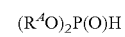 $(R^A O)_2 P(O) H$  Formula (XV)

 $R^A P(O)(OH) H$  Formula (XVI)

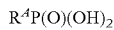 $R^A P(O)(OH)_2$  Formula (XVII)

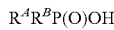 $R^A R^B P(O) OH$  Formula (XIII)

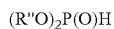 $(R'' O)_2 P(O) H$  Formula (XIX)

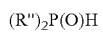 $(R'')_2 P(O) H$  Formula (XX)

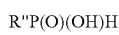 $R'' P(O)(OH) H$  Formula (XXI)

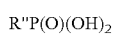 $R'' P(O)(OH)_2$  Formula (XXII)

wherein "$R^A$" and "$R^B$" may be the same or different and are selected from substituted or unsubstituted aryl or aryloxy groups and hydroxyl groups provided that not more than one of $R^A$ and $R^B$ is a hydroxyl group, and "$R^C$" and "$R^D$" may be the same or different and are selected from hydrocarbylene and hydrocarbenylene. $R^C$ and $R^D$ are preferably each independently, more preferably both, an arylene group.

Phenylphosphine is an example of Formula (XIV), diphenyl or diethyl phosphite or dimethylphosphite is an example of Formula (XV), phenylphosphinic acid $(C_6H_5)P(O)(OH)H$ is a an example of Formula (XVI), phenylphosphonic acid $(C_6H_5)P(O)(OH)_2$ is an example of Formula (XVII), and dimethylphosphinic acid $(CH_3)_2 P(O) OH$ is an example of Formula (XVIII).

In a preferred embodiment, the organophosphorus-containing compound, Component (A), corresponds to one of the following chemical Formulae (XXIII) to (XXVIII):

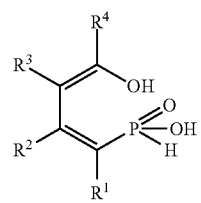  Formula (XXIII)

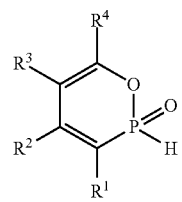  Formula (XXIV)

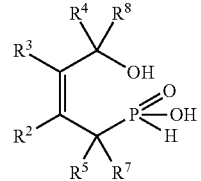  Formula (XXV)

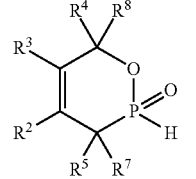  Formula (XXVI)

Formula (XXVII)

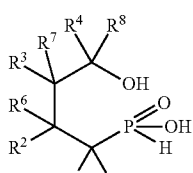

Formula (XXVIII)

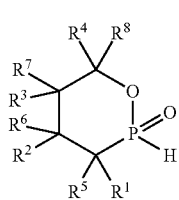

wherein each $R^1$ to $R^8$ is, independently, a hydrogen atom or a hydrocarbyl group that optionally may contain one or more heteroatoms such as O, N, S, P, or Si, provided that not more than 3 of $R^1$ to $R^4$ are hydrogen atoms and two or more of $R^1$ to $R^8$ may be joined to one another to form one or more cyclic groups. The total number of carbon atoms in $R^1$ to $R^8$ is preferably in the range from 6 to 100.

In a more preferred embodiment, the organophosphorus-containing compound, Component (A), corresponds to the following Formula (XXIX):

Formula (XXIX)

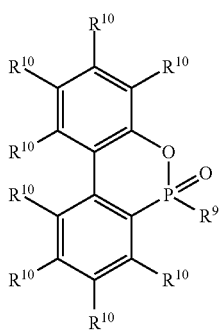

wherein $R^9$ represents H and each $R^{10}$ independently represents a hydrogen atom or a hydrocarbyl group that optionally may contain one or more heteroatoms such as O, N, S, P, or Si. Two or more of $R^{10}$ may be joined to one another to form one or more cyclic groups.

The above preferred embodiment organophosphorus-containing compounds are described in more detail in EP-A-806429.

The organophosphorus-containing compound, Component (A), is preferably 9,10-dihydro-9-oxa-10-phosphaphenanthrene-10-oxide (also known as "DOP"), such as "Sanko-HCA", which is commercially available from Sanko of Japan, or "Struktol Polydis™ PD 3710", which is commercially available from Schill & Seilacher of Germany; dimethylphosphite, diphenylphosphite, ethylphosphonic acid, diethylphosphinic acid, methyl ethylphosphinic acid, phenyl phosphonic acid, phenyl phosphinic acid, dimethylphosphinic acid, phenylphosphine, vinyl phosphoric acid; or mixtures thereof.

The organophosphorus-containing compound, Component (A), is preferably substantially free of bromine atoms, more preferably substantially free of halogen atoms.

Reaction of Component (A) with Component (B) to Form Compound (I)

To prepare Compound (I), Component (A) and Component (B) are first blended or mixed together to form a reactive composition. Then a sufficient temperature is applied to the reactive composition of Components (A) and (B) to initiate the reaction between the two components to form Compound (I).

Component (A) is mixed with Component (B) in a reaction vessel and the mixture is heated at an elevated temperature which is a temperature that is preferably below the decomposition temperature of the starting materials. Generally, the reaction temperature is greater than 25 degrees Celsius, preferably greater than 150 degrees Celsius, and more preferably greater than 170 degrees Celsius The reaction is preferably carried out for a period of time sufficient to a react the H—P═O, P—H, or P—OH moieties of Component (A) with the OR" moieties of Component (B). The time of reaction is typically from 30 minutes to 20 hours, preferably from 1 hour to 10 hours, and more preferably from 2 hours to 6 hours.

The reaction of the present invention is preferably carried out without the presence of water (generally the water is present in less than 5 wt percent, more preferable less than 3 wt percent and most preferable less than 1 wt percent) because water may tend to react with Component (A). Removal of alcohol and other volatile byproducts such as other solvents formed as a byproduct of this reaction generally helps drive the reaction to completion. The pressure in the reaction vessel is therefore preferably reduced to a pressure below atmospheric pressure, such as a pressure of 0.1 bar or less, to help drive off the alcohol or byproducts at a temperature below the above-mentioned lowest decomposition temperature. The reaction vessel may optionally be purged with a gas or volatile organic liquid to further assist in removing byproduct(s). The gas or volatile organic liquid is preferably inert to the contents of the reaction vessel.

Component (B) is usually dissolved in an organic solvent, well know to those skilled in the art, such as butanol, xylene, or Dowanol PM (trademark of The Dow Chemical Company); and part of the solvent can be removed either by heat or applying vacuum to the solution before the addition of Component (A). The order of charging of Component (A) and Component (B) into the reaction mixture is not important.

Components (A) and (B) are preferably combined at a weight ratio in the range from 10:1 to 1:10, preferably from 5:1 to 1:5, more preferably from 2:1 to 1:2, most preferably in the range from 1.1:1 to 1:1.1 based on total solids content of the composition.

If desired, other materials such as catalysts or solvents may be added to the reaction mixture of Component (A) and (B).

The phosphorous-containing product of the present invention, Compound (I), resulting from the reaction between Component (A) and Component (B) has a phosphorus content of preferably at least 4 weight-percent, and more preferably at least 6 weight-percent. The phosphorus content of Compound (I) generally ranges from 4 to 12 percent, preferably from 5 to 9 and more preferably from 6 to 8 weight percent. Component (I) is preferably substantially free of bromine atoms, and more preferably substantially free of halogen atoms.

Compound (I) has a Mettler softening point generally greater than 100° C. and preferably greater than 120° C.; and preferably less than 250° C. and more preferably less than 200° C. The product is preferably a solid at room temperature (about 25° C.) for better storing, shipping and handling.

Generally, the resulting Compound (I) from the reaction of Components (A) and (B) may be a blend of one or more of different oligomers.

Ignition Resistant Epoxy Resin Compositions

In one embodiment of the present invention, the phosphorus-containing compound, Compound (I), obtainable by reacting Component (A) with Component (B), as described above, may be used, as one component, of a curable (crosslinkable) phosphorus-containing flame resistant epoxy resin composition. In this embodiment, the curable phosphorus-containing flame-resistant epoxy resin composition comprises (i) the phosphorus-containing compound, Compound (I), according to the present invention, (ii) at least one epoxy resin such as those selected from halogen-free epoxies, phosphorus-free epoxies, brominated epoxies, and phosphorus-containing epoxies and mixtures thereof, including, but not limited to DEN 438, DER 330 (DEN and DER are trademarks of The Dow Chemical Company), epoxy functional polyoxazolidone containing compounds, cycloaliphatic epoxies, GMA/styrene copolymers, the reaction product of liquid epoxy resins (LER) and tetra bromo bisphenol A (TBBA) resins, DER 539, and the reaction product of DEN 438 and DOP resins; and optionally (iii) at least one curing agent. The curable flame-retardant epoxy resin composition optionally may contain at least one additional crosslinkable epoxy resin or a blend of two or more epoxy resins other than and different from component (ii) above. The curable flame resistant epoxy resin composition may also optionally contain at least one curing catalyst and at least one inhibitor. All of the above components may be blended or mixed together in any order to form the curable phosphorus-containing flame-retardant epoxy resin composition.

In another embodiment, Compound (I) may be first reacted with an epoxy compound to form a phosphorus-containing epoxy compound (herein referred to as an "epoxidized Compound (I)"), and then subsequently the epoxidized Compound (I) may be combined with at least one curing agent to form the curable flame-retardant epoxy resin composition. The curable flame-retardant epoxy resin composition of this embodiment optionally may contain at least one additional crosslinkable epoxy resin or a blend of two or more epoxy resins other than and different from the epoxidized Compound (I). This curable flame resistant epoxy resin composition may also optionally contain at least one curing catalyst and at least one inhibitor. This embodiment of the present invention directed to forming the epoxidized Compound (I) first, has an advantage of forming a low molecular weight epoxy compound that can be advanced to a higher molecular weight epoxy in a subsequent step or blended with other epoxy resins. The epoxidized Compound (I) may be obtainable by reacting (i) the above phosphorus-containing compound, Compound (I) with (ii) at least one epoxy compound having at least one epoxy group per molecule. For example, an epoxy resin having one epoxy group per molecule that can be used in the present invention may be epichlorohydrin. With epichlorohydrin, a lower molecular weight epoxidized Compound (I) may be obtained such as for example a resin having less than 700. In another embodiment, higher molecular weight epoxy resins such those having molecular weights of greater than 700 may be obtained by reacting (i) the above phosphorus-containing compound, Compound (I) with (ii) at least one epoxy compound having at least one, and preferably two or more, epoxy groups per molecule.

For example, the crosslinkable phosphorus-containing epoxy compound, epoxidized Compound (I), is obtainable by reacting the above-described phosphorus-containing compound, Compound (I), with at least one epoxy compound having more than 1, preferably at least 1.8, more preferably at least 2, epoxy groups per molecule, wherein the epoxy groups are 1,2-epoxy groups. In general, such polyepoxide compounds are a saturated or unsaturated aliphatic, cycloaliphatic, aromatic or heterocyclic compound which possess more than one 1,2-epoxy group. The polyepoxide compound can be substituted with one or more substituents such as lower alkyls. Such polyepoxide compounds are well known in the art. Illustrative polyepoxide compounds useful in the practice of the present invention are described in the *Handbook of Epoxy Resins* by H. E. Lee and K. Neville published in 1967 by McGraw-Hill, New York and U.S. Pat. No. 4,066,628.

The epoxidized Compound (I) which contains a phosphorus element can be used to form curable epoxy compositions with the addition of a crosslinker and, optionally, a catalyst to produce the curable flame resistant epoxy resin compositions.

The curable flame resistant epoxy resin compositions prepared according to the present invention whether made either by reacting a mixture of Compound (I), an epoxy resin and a curing agent; or by reacting an epoxidized Compound (I) with a curing agent, may be used to make prepregs, which, in turn, may be used to make laminates and circuit boards useful in the electronics industry. The curable composition may also be used to coat metallic foils such as copper foils to make resin coated copper foils for a so call build up technology.

Any of the epoxy resins which can be used in the above compositions to practice of the present invention include polyepoxides having the following general Formula (XXX):

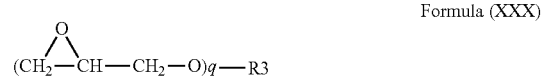

Formula (XXX)

wherein "R3" is substituted or unsubstituted aromatic, aliphatic, cycloaliphatic or heterocyclic group having a valence of "q", "q" preferably having an average value of from 1 to less than about 8. Examples of the polyepoxide compounds useful in the present invention include the diglycidyl ethers of the following compounds: resorcinol, catechol, hydroquinone, bisphenol, bisphenol A, bisphenol AP (1,1-bis(4-hydroxylphenyl)-1-phenyl ethane), bisphenol F, bisphenol K, tetrabromobisphenol A, phenol-formaldehyde novolac resins, alkyl substituted phenol-formaldehyde resins, phenol-hydroxybenzaldehyde resins, cresol-hydroxybenzaldehyde resins, dicyclopentadiene-phenol resins, dicyclopentadiene-substituted phenol resins tetramethylbiphenol, tetramethyl-tetrabromobiphenol, tetramethyltribromobiphenol, tetrachlorobisphenol A, and any combination thereof.

Examples of particular polyepoxide compounds useful in the present invention include a diglycidyl ether of bisphenol A having an epoxy equivalent weight (EEW) between 177 and 189 sold by The Dow Chemical Company under the trademark D.E.R. 330; the halogen-free epoxy-terminated polyoxazolidone resins disclosed in U.S. Pat. No. 5,112,932, phosphorus element containing compounds disclosed in U.S. Pat. No. 6,645,631; cycloaliphatic epoxies; and copolymers of glycidyl methacrylate ethers and styrene.

Preferred polyepoxide compounds include epoxy novolacs, such as D.E.N. 438 or D.E.N. 439 (trademarks of The Dow Chemical Company); cresole epoxy novolacs such as QUATREX 3310, 3410 and 3710 available from Ciba Geigy; trisepoxy compounds, such as TACTIX 742 (trademark of Ciba Geigy Corporation of Basel, Switzerland); epoxidized bisphenol A novolacs, dicyclopentadiene phenol epoxy novolacs; glycidyl ethers of tetraphenolethane; diglycidyl ethers of bisphenol-A; diglycidyl ethers of bisphenol-F; and diglycidyl ethers of hydroquinone.

In one embodiment, the most preferred epoxy compounds are epoxy novolac resins (sometimes referred to as epoxidized novolac resins, a term which is intended to embrace both epoxy phenol novolac resins and epoxy cresol novolac resins). Such epoxy novolac resin compounds have the general chemical structural formula illustrated by Formula (XXXI) as follows:

pared according to U.S. Pat. No. 6,645,631, and optionally (iii) at least one curing agent; or the curable flame retardant epoxy resin composition may be formed by blending (i) an epoxidized Compound (I), at least one crosslinkable phosphorus-containing epoxy compound prepared according to U.S. Pat. No. 6,645,631, and (iii) at least one curing agent. The curable epoxy resin compositions may, optionally, contain at least one crosslinkable epoxy resin other than the crosslinkable phosphorus-containing epoxy compounds in (ii) above.

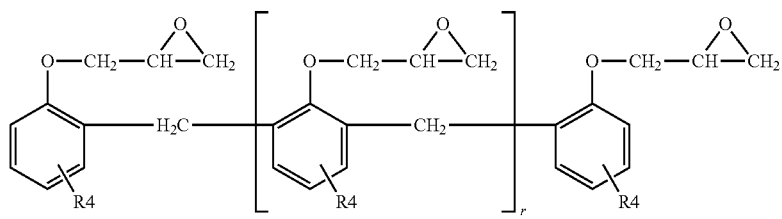

Formula (XXXI)

wherein "R4" is hydrogen or a $C_1$-$C_3$ alkyl, for example, methyl; and "r" is 0 or an integer from 1 to 10. "n" preferably has an average value of from 0 to 5. The preferred epoxy novolac resin is when "R4" is preferably a hydrogen atom in the above Formula (XXXI).

Epoxy novolac resins (including epoxy cresol novolac resins) are readily commercially available, for example under the trade names D.E.N. (trademark of The Dow Chemical Company), and QUATREX and TACTIX 742 (trademarks of Ciba Geigy). The materials of commerce generally comprise mixtures of various species of the above Formula (XXXI) and a convenient way of characterizing such mixtures is by reference to the average, r', of the values of r for the various species. Preferred epoxy novolac resins for use in accordance with the present invention are those in which r' has a value of from 0 to 10, more preferably from 1 to 5.

Additional examples of epoxy-containing compounds useful in the present invention are the reaction products of an epoxy compound containing at least two epoxy groups and a chain extender as described in WO 99/00451. The preferred reaction product described in WO 99/00451 useful in the present invention is an epoxy-polyisocyanate adduct or an epoxy-terminated polyoxazolidone as described in U.S. Pat. No. 5,112,932. The isocyanate compounds as chain extenders include for example diphenylmethane diisocyanate (MDI), toluene diisocyanate (TDI) and isomers thereof.

The polyepoxide useful in the present invention is preferably substantially free of bromine atoms, and more preferably substantially free of halogen atoms.

An example of polyepoxides that are useful in the present invention and that are substantially free of halogen atoms are the phosphorus-containing epoxy resins described in U.S. Pat. No. 6,645,631. The polyepoxides disclosed in U.S. Pat. No. 6,645,631 are the reaction products of an epoxy compound containing at least two epoxy groups and a reactive phosphorus-containing compound such as 3,4,5,6-dibenzo-1,2-oxaphosphane-2-oxide (DOP), or 10-(2',5'-dihydroxyphenyl)-9,10-dihydro-9-oxa-10-phosphaphenanthrene-10-oxide (DOP-HQ).

As described above, a curable flame resistant epoxy resin composition may be formed by blending (i) the phosphorus-containing product, Compound (I), obtainable by reacting Component (A) with Component (B), (ii) at least one crosslinkable phosphorus-containing epoxy compound pre- Although it is preferred that the polyepoxide useful in the present invention be substantially free of bromine atoms, and more preferably substantially free of halogen atoms, in some applications a halogen containing epoxy resin composition may be desired. In such cases, the polyepoxide used in the present invention may be for example a brominated epoxy compound such as a brominated epoxy resin having an EEW of 400 to 450 sold by The Dow Chemical Company under the trademark of DER 530.

With any of the compositions above where an epoxy resin is present, any number of crosslinking agents or co-crosslinking agents may be used. Suitable co-crosslinkers that may optionally be present in combination with the phosphorus-containing epoxy compounds according to the present invention include, for example, are the multifunctional co-crosslinkers described in numerous references such as *Vol. 6 Encyclopedia of Poly. Sci. & Eng.*, "Epoxy Resins" at 348-56 (J. Wiley & Sons 1986).

Other preferred co-crosslinkers are described in WO 98/31750. The co-crosslinkers include, for example, copolymers of styrene and maleic anhydride having a molecular weight ($M_w$) in the range of from 1500 to 50,000 and an anhydride content of more than 15 percent. Commercial examples of these materials include SMA 1000, SMA 2000, and SMA 3000 and SMA 4000 having styrene-maleic anhydride ratios of 1:1, 2:1, 3:1 and 4:1, respectively, and having molecular weights ranging from 6,000 to 15,000, which are available from Elf Atochem S.A.

Other preferred co-crosslinkers useful in the present invention include hydroxyl-containing compounds such as those represented by the following Formula (XXXII):

Formula (XXXII)

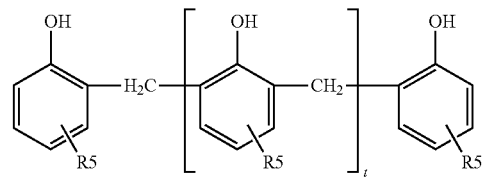

wherein "R5" is hydrogen or an alkyl group having from 1 to 20, preferably from 1 to 10, and more preferably 2 to 5, carbon atoms and "t" is an integer of from 0 to 20, preferably from 1 to 10 and more preferably from 2 to 5.

Commercially available products having the above Formula (XXXII) include, for example, PERSTORP 85.36.28, which is a phenolic resin obtained from phenol and formaldehyde having an average Mettler softening point of 103° C., melt viscosity at 150° C.=1.2 Pa·s and a functionality of 6 to 7. Another example includes DURITE SD 1731 from Borden Chemical of USA.

Other phenolic functional materials include compounds which form a phenolic crosslinking agent having a functionality of at least 2 upon heating. Some examples of these compounds are benzoxazine groups-containing compounds. Examples of compounds which form a phenolic crosslinking agent upon heating include phenolic species obtained from heating benzoxazine, for example as illustrated in the following chemical equation:

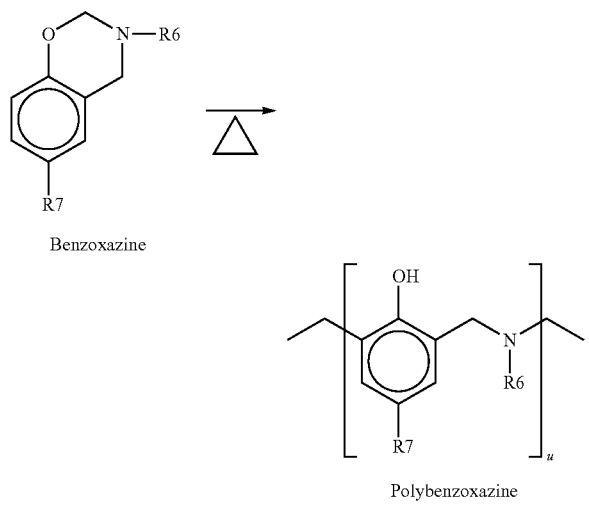

wherein "u" is greater than 1 and preferably up to about 100,000; and wherein "R6" and "R7" may be, independently and separately, the same or different hydrogen, an allyl group from $C_1$-$C_{10}$ such as methyl, a $C_6$-$C_{20}$ aromatic group such as phenyl or a $C_4$-$C_{20}$ cycloaliphatic group such as cyclohexane.

Examples of the above compounds also include benzoxazine of phenolphthalein, benzoxazine of bisphenol-A, benzoxazine of bisphenol-F, benzoxazine of phenol novolac, and mixtures thereof. Other compounds useful in the present invention are described in WO 00/27921, and U.S. Pat. No. 6,545,631. A mixture of these compounds and Formula (XXXII) may also be used in the present invention.

The multi-functional phenolic crosslinker is preferably used in the epoxy resin composition in an amount of from 50 percent to 150 percent of the stoichiometric amount needed to cure the epoxy resins and more preferably from 75 percent to 125 percent of the stoichiometric amount needed to cure the epoxy resins, even more preferably from 85 percent to 110 percent of the stoichiometric amount needed to cure the epoxy resins.

When a co-crosslinker is used in the present invention, the co-crosslinker is present in an amount to crosslink less than 40 percent of the stoichiometric amount needed to cure the epoxy resin.

Any of the curable compositions of the present invention descried above may comprise a catalyst. Examples of suitable catalyst materials useful in the present invention include compounds containing amine, phosphine, ammonium, phosphonium, arsonium or sulfonium moieties or mixtures thereof. Particularly preferred catalysts are heterocyclic nitrogen-containing compounds.

The catalysts (as distinguished from co-crosslinkers) preferably contain on average no more than about 1 active hydrogen moiety per molecule. Active hydrogen moieties include hydrogen atoms bonded to an amine group, a phenolic hydroxyl group, or a carboxylic acid group. For instance, the amine and phosphine moieties in catalysts are preferably tertiary amine or phosphine moieties; and the ammonium and phosphonium moieties are preferably quaternary ammonium and phosphonium moieties.

Among preferred tertiary amines that may be used as catalysts are those mono- or polyamines having an open-chain or cyclic structure which have all of the amine hydrogen replaced by suitable substituents, such as hydrocarbyl radicals, and preferably aliphatic, cycloaliphatic or aromatic radicals.

Examples of these amines include, among others, 1,8-diazabicyclo(5.4.0)undec-7-en (DBU), methyl diethanol amine, triethylamine, tributylamine, dimethyl benzylamine, triphenylamine, tricyclohexyl amine, pyridine and quinoline. Preferred amines are the trialkyl, tricycloalkyl and triaryl amines, such as triethylamine, triphenylamine, tri-(2,3-dimethylcyclohexyl)amine, and the alkyl dialkanol amines, such as methyl diethanol amines and the trialkanolamines such as triethanolamine Weak tertiary amines, for example, amines that in aqueous solutions give a pH less than 10 in aqueous solutions of 1 M concentration, are particularly preferred. Especially preferred tertiary amine catalysts are benzyldimethylamine and tris-(dimethylaminomethyl)phenol.

Examples of suitable heterocyclic nitrogen-containing catalysts include those described in U.S. Pat. No. 4,925,901. Preferable heterocyclic secondary and tertiary amines or nitrogen-containing catalysts which can be employed herein include, for example, imidazoles, benzimidazoles, imidazolidines, imidazolines, oxazoles, pyrroles, thiazoles, pyridines, pyrazines, morpholines, pyridazines, pyrimidines, pyrrolidines, pyrazoles, quinoxalines, quinazolines, phthalozines, quinolines, purines, indazoles, indoles, indolazines, phenazines, phenarsazines, phenothiazines, pyrrolines, indolines, piperidines, piperazines and combinations thereof. Especially preferred are the alkyl-substituted imidazoles; 2,5-chloro-4-ethyl imidazole; and phenyl-substituted imidazoles, and mixtures thereof. Even more preferred are N-methylimidazole; 2-methylimidazole; 2-ethyl-4-methylimidazole; 1,2-dimethylimidazole; and 2-methylimidazole and mixtures thereof. Especially preferred is 2-phenylimidazole.

Preferably, a Lewis acid is also employed in any of the curable epoxy resin compositions of the present invention described above, especially when the catalyst is particularly a heterocyclic nitrogen-containing compound.

Examples of heterocyclic nitrogen-containing catalysts, which are preferably used in combination with Lewis acids are those described in EP A 526488, EP A 0458502, and GB A 9421405.3.

The Lewis acids useful in the present invention include for example one or a mixture of two or more halides, oxides, hydroxides and alkoxides of zinc, tin, titanium, cobalt, manganese, iron, silicon, aluminum, and boron, for example Lewis acids of boron, and anhydrides of Lewis acids of boron, for example boric acid, metaboric acid, optionally substituted boroxines (such as trimethoxyboroxine), optionally substituted oxides of boron, alkyl borates, boron halides, zinc halides (such as zinc chloride) and other Lewis acids that tend to have a relatively weak conjugate base. Preferably the Lewis acid is a Lewis acid of boron, or an anhydride of a Lewis acid of boron, for example boric acid, metaboric acid, an optionally substituted boroxine (such as trimethoxy boroxine, trimethyl boroxine or triethyl boroxine), an optionally substituted oxide of boron, or an alkyl borate. The most preferred Lewis acid is boric acid. These Lewis acids are very effective in curing epoxy resins when combined with the heterocyclic nitrogen-containing compounds, referred to above.

The Lewis acids and amines can be combined before mixing into the formulation or by mixing with the catalyst in situ, to make a curing catalyst combination.

The amount of the Lewis acid employed is preferably at least 0.1 mole of Lewis acid per mole of heterocyclic nitrogen compound, more preferably at least 0.3 mole of Lewis acid per mole of heterocyclic nitrogen-containing compound.

The curable compositions of the present invention may optionally have boric acid and/or maleic acid present as a cure inhibitor as described in U.S. Pat. No. 5,308,895 and U.S. Pat. No. 5,314,720. In that case, the curing agent is preferably a polyamine or polyamide, such as described in U.S. Pat. No. 4,925,901.

The curable compositions of the present invention may also optionally contain one or more additional flame retardant additives including, for example, red phosphorus, encapsulated red phosphorus or liquid or solid phosphorus-containing compounds, for example, "EXOLIT OP 930", EXOLIT OP 910 from Clariant GmbH and ammonium polyphosphate such as "EXOLIT 700" from Clariant GmbH, a phosphite, or phosphazenes; nitrogen-containing fire retardants and/or synergists, for example melamines, melem, cyanuric acid, isocyanuric acid and derivatives of those nitrogen-containing compounds; halogenated flame retardants and halogenated epoxy resins (especially brominated epoxy resins); synergistic phosphorus-halogen containing chemicals or compounds containing salts of organic acids; inorganic metal hydrates such as $Sb_2O_3$, $Sb_3O_5$, aluminum trihydroxide and magnesium hydroxide such as "ZEROGEN 30" from Martinswerke GmbH of Germany, and more preferably, an aluminum trihydroxide such as "MARTINAL TS-610" from Martinswerke GmbH of Germany; boron-containing compounds; antimony-containing compounds; silica and combinations thereof. Examples of suitable additional flame retardant additives are given in a paper presented at "Flame retardants—101 Basic Dynamics—Past efforts create future opportunities," Fire Retardants Chemicals Association, Baltimore Marriot Inner Harbour Hotel, Baltimore Md., Mar. 24-27, 1996.

When additional flame retardants which contain a halogen is used in the composition of the present invention, the halogen-containing flame retardants are present in amounts such that the total halogen content in the epoxy resin composition is less than 10 wt. percent, more preferably less than 5 wt. percent, and even more preferably less than 1 wt. percent.

When additional flame retardants which contain phosphorus are present in the composition of the present invention, the phosphorus-containing flame retardants are preferably present in amounts such that the total phosphorus content of the epoxy resin composition is from 0.2 wt. percent to 5 wt. percent.

The curable compositions of the present invention may also optionally contain other additives of a generally conventional type including for example, stabilizers, other organic or inorganic additives, pigments, wetting agents, flow modifiers, UV light blockers, and fluorescent additives. These additives can be present in amounts of from 0 to 5 weight-percent and is preferably present in amounts less than 3 weight percent. Examples of suitable additives are also described in U.S. Pat. No. 5,066,735 and in C.A. Epoxy Resins—Second Ed. at pages 506-512 (Mercel Dekker, Inc. 1988).

The curable compositions of the present invention can be produced by mixing all the components together in any order. Compositions of the present invention may also be produced by preparing a first composition comprising an epoxy resin, and a second composition comprising a curing agent. The first epoxy resin composition may contain Compound (I) and an epoxy resin; or it may be simply an epoxidized Compound (I). All other optional or desired components, such as a curing catalyst or inhibitor, may be present in the same composition, or some may be present in the first, and some in the second. The first composition is then mixed with the second composition, and cured to produce a flame resistant epoxy resin.

The flame resistant epoxy resin is preferably substantially free of bromine atoms, and more preferably substantially free of halogen atoms, as the expression "substantially free" is defined above.

The compositions of the present invention can be used to make composite materials by techniques well-known in the industry, such as by pultrusion, molding, encapsulation, or coating. The present invention is particularly useful for making B-staged prepregs, laminates, bonding sheets, and resin coated copper foils by well known techniques in the industry, as described in the background sections of EP-A-787161 and U.S. Pat. No. 5,314,720.

Benzoxazine Ring-Containing Compounds

In another embodiment of the present invention, the phosphorus-containing product, Compound (I), obtainable by reacting Component (A) with Component (B) may be used to make a benzoxazine ring-containing compound.

In this embodiment, the benzoxazine compound is obtainable by reacting (i) the above phosphorus-containing compound, Compound (I), having a phenolic functionality with (ii) a primary amine and (iii) a formaldehyde. These phosphorus containing benzoxazine ring-containing compounds can either:

(a) be used per se and self crosslink at elevated temperatures, such as from 100° C. to 250° C., to form a highly crosslinkable network which has flame resistant properties; or (b) be blended with epoxy resins or other thermosetting compositions and cured at the above elevated temperatures to form a flame resistant hybrid crosslink network; or (c) be blended with thermoplastics systems (for example, polystyrene, polyethylene, polypropylene, polyphenylenoxides (PPO)) to form a flame resistant hybrid crosslink network; or (d) be blended with thermoplastic resin (such as PPO) and a thermosetting resin (such as epoxy and curing agent) to form a hybrid system.

As an illustration of the above embodiment, a benzoxazine may be formed in accordance with the following general chemical reaction:

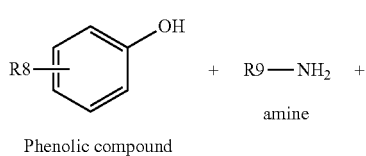

Phenolic compound

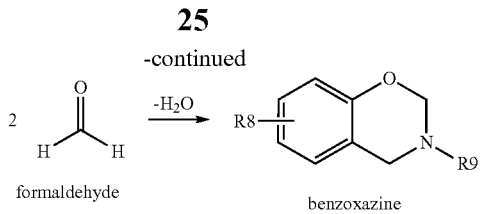

formaldehyde    benzoxazine

In a similar reaction as above, the phenolic-containing Compound (I) of the present invention is reacted with an amine and a formaldehyde to form a benzoxazine ring-containing compound.

In another embodiment, if Compound (I) has an amine functionality, then a known phenolic compound can be reacted with the amine containing Compound (I) and a formaldehyde to form the benzoxazine ring containing compound.

The molar ratios of the three components used in the present invention are usually 1 mole of phenolic OH groups, 1 mole of amine groups and 2 moles of formaldehyde groups as illustrated in the above general reaction. Other ratios between the above components may be used. A mixture of different amine compounds may be used.

The amines useful in the present invention include for example aniline, n-butyl amine, 1,4-amino phenol, other primary amines, and mixtures thereof.

The phenolics useful in the present invention include for example bisphenol A, 2-allyl phenol, 4,4'-methylene diphenol, other mono phenols, and polyphenols, and mixtures thereof.

Thermolabile Group-Containing Compounds

In another embodiment of the present invention, the phosphorus-containing product, Compound (I), obtainable by reacting Component (A) with Component (B) may be used to make a thermolabile group-containing compound.

In this embodiment, the phosphorus-containing compound with a thermolabile group may be obtainable by reacting (i) the above phosphorus-containing compound, Compound (I) having a phenolic or an amine functionality with (ii) a thermolabile group containing compound, such as a compound having t-butyloxycarbonyl groups. These modified phosphorus compounds are stable at ambient temperature and its thermolabile groups degrade at elevated temperature such as from 100° C. to 250° C., leading to gas generation. These modified phosphorus compounds can be blended to different thermosetting systems to generate gas bubbles leading to encapsulation of gas in the crosslinked systems having lower dielectric constant for example 10 percent lower than its initial value without the modified phosphorous compound; and loss factor that is 10 percent lower or products having lower weight for example 10 weight lower when the processing temperature is well controlled as described in U.S. patent application Ser. No. 10/456,127 filed June, 2003 entitled "Nanoporous Laminates".

The thermolabile group containing compounds useful in the present invention include for example a dicarbonate and its derivatives, a carbazate and its derivatives, and other compounds containing tert-butyl carbonate. Examples of compounds containing thermolabile group are, but not limited to, di-tert-butyl dicarbonate, di-tert-amyl dicarbonate, diallyl pyrocarbonate, diethyl pyrocarbonate, dimethyl dicarbonate, dibenzyl dicarbonate, tert-butyl carbazate and mixtures thereof. The tert-butyl carbonate thermolabile group is advantageously stable to many nucleophiles and is not hydrolyzed under basic conditions, but it may be easily cleaved under mid-acidic conditions or by thermolysis.

The molar ratios of the two components used in the present invention are usually 1 mole of active hydrogen group to 1 mole of thermolabile group to form the phosphorus-containing, thermolabile group containing compound of the present invention.

Flame Resistant Polyurethane

In another embodiment of the present invention, the phosphorus-containing product, Compound (I), obtainable by reacting Component (A) with Component (B) is used to make phosphorus-containing polyols which are, in turn, useful for making flame resistant polyurethane.

The phosphorus-containing polyols of the present invention are preferably prepared by reacting (i) an alkylene oxide, such as ethylene oxide, propylene oxide, butylene oxide or a combination thereof, with (ii) the phosphorus-containing compound, Compound (I), according to the present invention. The resultant phosphorus-containing polyol product of the present invention preferably has from 1 to 8, and more preferably 2 to 6, active hydrogen atoms.

A catalyst may be used in the above reaction to form the phosphorous-containing polyols. Catalysis for the above reaction can be either anionic or cationic. Suitable catalysts include KOH, CsOH, boron trifluoride, a double cyanide complex (DMC) catalyst such as zinc hexacyanocobaltate, and the catalysts described in U.S. Pat. No. 6,201,101.

The phosphorus-containing polyol of the present invention may be used alone or in combination with one or more other know polyols to form a base polyol composition which may be reacted with a polyisocyanate to form a polyurethane. The properties of the final polyurethane product will depend on the nature of the various polyols used in the polyol composition.

The phosphorus-containing polyol or blend thereof employed to make polyurethane resin depends upon the end use of the polyurethane product to be produced. The molecular weight or hydroxyl number of the base polyol may thus be selected so as to result in flexible, semi-flexible, integral-skin or rigid foams, elastomers or coatings, or adhesives when the polyol produced from the base polyol is converted to a polyurethane product by reaction with an isocyanate, and depending on the end product in the presence of a blowing agent. The hydroxyl number and molecular weight of the polyol or polyols employed can vary accordingly over a wide range. In general, the hydroxyl number of the polyols employed may range from 20 to 800.

In the production of a flexible polyurethane foam, the polyol is preferably a polyether polyol and/or a polyester polyol. The polyol generally has an average functionality ranging from 2 to 5, preferably 2 to 4, and an average hydroxyl number ranging from 20 to 100 mg KOH/g, preferably from 20 to 70 mg KOH/g. As a further refinement, the specific foam application will likewise influence the choice of base polyol. As an example, for molded foam, the hydroxyl number of the base polyol may be on the order of 20 to 60 with ethylene oxide (EO) capping, and for slabstock foams the hydroxyl number may be on the order of 25 to 75 and is either mixed feed EO/PO (propylene oxide) or is only slightly capped with EO or is 100 percent PO based. For elastomer applications, it will generally be desirable to utilize relatively high molecular weight base polyols, from 2,000 to 8,000, having relatively low hydroxyl numbers, for example, 20 to 50.

Typically, polyols suitable for preparing rigid polyurethanes include those having an average molecular weight of 100 to 10,000 and preferably 200 to 7,000. Such polyols also advantageously have a functionality of at least 2, preferably 3, and up to 8, preferably up to 6, active hydrogen atoms per molecule. The polyols used for rigid foams generally have a hydroxyl number of 200 to 1,200 and more preferably from 300 to 800.

For the production of semi-rigid foams, it is preferred to use a trifunctional polyol with a hydroxyl number of 30 to 80.

A flame resistant polyurethane resin is obtainable by reacting (i) at least one phosphorus-containing polyol according to the present invention, alone or, optionally, in combination with one or more polyols conventionally used to make polyurethanes other than the phosphorus-containing polyol of the present invention, with (ii) a compound having more than one isocyanate group per molecule. The isocyanates which may be used with the polyols of the present invention include aliphatic, cycloaliphatic, arylaliphatic and aromatic isocyanates and mixtures thereof. Aromatic isocyanates, especially aromatic polyisocyanates, are preferred.

Examples of suitable aromatic isocyanates include the 4,4'-, 2,4' and 2,2'-isomers of diphenylmethane diisocyanate (MDI), blends thereof and polymeric and monomeric MDI blends toluene-2,4- and 2,6-diisocyanates (TDI), m- and p-phenylenediisocyanate, chlorophenylene-2,4-diisocyanate, diphenylene-4,4'-diisocyanate, 4,4'-diisocyanate-3,3'-dimehtyldiphenyl, 3-methyldiphenyl-methane-4,4'-diisocyanate and diphenyletherdiisocyanate and 2,4,6-triisocyanatotoluene and 2,4,4'-triisocyanatodiphenylether and mixtures thereof. The hydrogenated products of these isocyanate compounds can be used as well.

Mixtures of isocyanates may be used, such as the commercially available mixtures of 2,4- and 2,6-isomers of toluene diisocynates. A crude polyisocyanate may also be used in the practice of this invention, such as crude toluene diisocyanate obtained by the phosgenation of a mixture of toluene diamine or the crude diphenylmethane diisocyanate obtained by the phosgenation of crude methylene diphenylamine. TDI/MDI blends may also be used. MDI or TDI based prepolymers can also be used, made either with different polyols. Isocyanate-terminated prepolymers are prepared by reacting an excess of polyisocyanate with polyols, including aminated polyols or imines/enamines thereof, or polyamines.

Examples of aliphatic polyisocyanates include ethylene diisocyanate, 1,6-hexamethylene diisocyanate, isophorone diisocyanate, cyclohexane 1,4-diisocyanate, 4,4'-dicyclohexylmethane diisocyanate, saturated analogues of the above mentioned aromatic isocyanates and mixtures thereof.

The preferred polyisocyanates for the production of rigid or semi-rigid foams are polymethylene polyphenylene isocyanates, the 2,2',2,4' and 4,4' isomers of diphenylmethylene diisocyanate and mixtures thereof. For the production of flexible foams, the preferred polyisocyanates are the toluene-2,4- and 2,6-diisocyanates or MDI or combinations of TDI/MDI or prepolymers made therefrom.

Isocyanate tipped prepolymer based on the phosphorus-containing polyol of the present invention can also be used in the polyurethane formulation. It is thought that using such polyols in a polyol isocyanate reaction mixture will reduce/eliminate the presence of unreacted isocyanate monomers. This is especially of interest with volatile isocyanates such as TDI and/or aliphatic isocyanates in coating and adhesive applications since it improves handling conditions and workers safety.

For rigid foam, the organic polyisocyanates and the isocyanate reactive compounds are reacted in such amounts that the isocyanate index, defined as the number or equivalents of NCO groups divided by the total number of isocyanate reactive hydrogen atom equivalents multiplied by 100, ranges from 80 to less than 500, preferably from 90 to 100 in the case of polyurethane foams, and from 100 to 300 in the case of combination polyurethane-polyisocyanurate foams. For flexible foams, this isocyanate index is generally between 50 and 120 and preferably between 75 and 110.

For elastomers, coating and adhesives the isocyanate index is generally between 80 and 125, preferably between 100 to 110.

For producing a polyurethane-based foam, a blowing agent is generally required. In the production of flexible polyurethane foams, water is preferred as a blowing agent. The amount of water is preferably in the range of from 0.5 to 10 parts by weight, more preferably from 2 to 7 parts by weight based on 100 parts by weight of the polyol. Carboxylic acids or salts are also used as blowing agents.

In the production of rigid polyurethane foams, the blowing agent includes water, and mixtures of water with a hydrocarbon or carbon dioxide, or a fully or partially halogenated aliphatic hydrocarbon. The amount of water is preferably in the range of from 2 to 15 parts by weight, more preferably from 2 to 10 parts by weight based on 100 parts of the polyol. With excessive amount of water, the curing rate becomes lower, the blowing process range becomes narrower, the foam density becomes lower, or the moldability becomes worse. The amount of hydrocarbon, the hydrochlorofluorocarbon, or the hydrofluorocarbon to be combined with the water is suitably selected depending on the desired density of the foam, and is preferably not more than 40 parts by weight, more preferably not more than 30 parts by weight based on 100 parts by weight of the polyol. When water is present as an additional blowing agent, it is generally present in an amount from 0.5 to 10, preferably from 0.8 to 6 and more preferably from 1 to 4 and most preferably from 1 to 3 parts by total weight of the total polyol composition.

In addition to the foregoing components, it is often desirable to employ certain other ingredients in preparing polyurethane polymers. Among these additional ingredients are surfactants, preservatives, flame retardants, colorants, antioxidants, reinforcing agents, stabilizers and fillers.

In making polyurethane foam, it is generally preferred to employ an amount of a surfactant to stabilize the foaming reaction mixture until it cures. Such surfactants advantageously comprise a liquid or solid organosilicone surfactant. Other surfactants include polyethylene glycol ethers of long-chain alcohols, tertiary amine or alkanolamine salts of long-chain alkyl acid sulfate esters, alkyl sulfonic esters and alkyl arylsulfonic acids. Such surfactants are employed in amounts sufficient to stabilize the foaming reaction mixture against collapse and the formation of large, uneven cells. Typically, 0.2 to 3 parts of the surfactant per 100 parts by weight total polyol (b) are sufficient for this purpose.

One or more catalysts for the reaction of the polyol (and water, if present) with the polyisocyanate can be used. Any suitable urethane catalyst may be used, including tertiary amine compounds, amines with isocyanate reactive groups and organometallic compounds and mixtures thereof. Preferably the reaction is carried out in the absence of an amine or an organometallic catalyst or a reduced amount as described above. Exemplary tertiary amine compounds include triethylenediamine, N-methylmorpholine, N,N-dimethylcyclohexylamine, pentamethyldiethylenetriamine, tetramethylethylenediamine, bis(dimethylaminoethyl)ether, 1-methyl-4-dimethylaminoethyl-piperazine, 3-methoxy-N-dimethylpropylamine, N-ethylmorpholine, dimethylethanolamine, N-cocomorpholine, N,N-dimethyl-N',N'-dimethyl isopropylpropylenediamine, N,N-diethyl-3-diethylamino-propylamine and dimethylbenzylamine. Exemplary organometallic catalysts include organomercury, organolead, organoferric and organotin catalysts, with organotin catalysts being preferred among these. Suitable tin catalysts include stannous chloride, tin salts of carboxylic acids such as dibutyltin di-laurate, as well as other organometallic compounds such as are disclosed in U.S. Pat. No. 2,846,408. A catalyst for the trimerization of polyisocyanates, resulting in a polyisocyanurate, such as an alkali metal alkoxide may also optionally be employed herein. The amount of amine catalysts can vary from 0.02 to 5 percent in the formulation or organometallic catalysts from 0.001 to 1 percent in the formulation can be used.

A crosslinking agent or a chain extender may be added, if necessary. The crosslinking agent or the chain extender includes low-molecular polyhydric alcohols such as ethylene glycol, diethylene glycol, 1,4-butanediol, and glycerin; low-molecular amine polyols such as diethanolamine and triethanolamine; and polyamines such as ethylene diamine, xlylenediamine, and methylene-bis(o-chloroaniline); and mixtures thereof. The use of such crosslinking agents or chain extenders is known in the art as disclosed in U.S. Pat. Nos. 4,863,979 and 4,963,399; and EP 549,120.

Especially when preparing rigid foams for use in construction, an additional flame retardant may be included as an additive. Any known liquid or solid flame retardant can be used with the polyols of the present invention. Generally such flame retardant agents are halogen-substituted phosphates and inorganic flame proofing agents. Common halogen-substituted phosphates are tricresyl phosphate, tris(1,3-dichloropropyl phosphate, tris(2,3-dibromopropyl)phosphate and tetrakis(2-chloroethyl)ethylene diphosphate. Inorganic flame retardants include red phosphorous, aluminum oxide hydrate, antimony trioxide, ammonium sulfate, expandable graphite, urea or melamine cyanurate or mixtures of at least two flame retardants. When there is a desire to minimize the amount of halogen in the formulation, the inorganic flame retardants are preferred.

The applications for polyurethane foams produced by the present invention are those known in the industry. For example rigid foams are used in the construction industry and for insulation for appliances and refrigerators. Flexible foams and elastomers find use in applications such as furniture, shoe soles, automobile seats, sun visors, steering wheels, armrests, door panels, noise insulation parts and dashboards.

Processing for producing polyurethane products are well known in the art. In general components of the polyurethane-forming reaction mixture may be mixed together in any convenient manner, for example by using any of the mixing equipment described in the prior art for the purpose such as described in *Polyurethane Handbook*, by G. Oertel, Hanser, publisher.

The polyurethane products are either produced continuously or discontinuously, by injection, pouring, spraying, casting, calendering; these are made under free rise or molded conditions, with or without release agents, in-mold coating, or any inserts or skin put in the mold. In case of flexible foams, those can be mono- or dual-hardness.

For producing rigid foams, the known one-shot prepolymer or semi-prepolymer techniques may be used together with conventional mixing methods including impingement mixing. The rigid foam may also be produced in the form of slabstock, moldings, cavity filling, sprayed foam, frothed foam or laminates with other material such as paper, metal, plastics or wood-board. Flexible foams are either free rise and molded while microcellular elastomers are usually molded.

The flame resistant polyurethane resin according to this invention is preferably substantially free of bromine atoms, and more preferably substantially free of halogen atoms, as the expression "substantially free" is defined above.

Ignition-Resistant Thermoplastic Resins

In another embodiment of the present invention, the phosphorus-containing product, Compound (I), obtainable by reacting Component (A) with Component (B) is used to make phosphorus-containing ignition resistant thermoplastic resins.

A halogen-free ignition-resistant thermoplastic resin composition are obtainable by blending (i) the phosphorus-containing compound, Compound (I), according to the present invention with (ii) at least one thermoplastic resin.

Typical thermoplastic polymers include, but are not limited to, polymers produced from vinyl aromatic monomers and hydrogenated versions thereof, including both diene and aromatic hydrogenated versions, including aromatic hydrogenation, such as styrene-butadiene block copolymers, polystyrene (including high impact polystyrene), acrylonitrile-butadiene-styrene (ABS) copolymers, and styrene-acrylonitrile copolymers (SAN); polycarbonate (PC), ABS/PC compositions, polyethylene terephthalate, epoxy resins, hydroxy phenoxy ether polymers (PHE) such as those taught in U.S. Pat. Nos. 5,275,853; 5,496,910; 3,305,528; ethylene vinyl alcohol copolymers, ethylene acrylic acid copolymers, polyolefin carbon monoxide interpolymers, chlorinated polyethylene, polyolefins (for example, ethylene polymers and propylene polymers, such as polyethylene, polypropylene, and copolymers of ethylene and/or propylene with each other or with an α-olefin having at least 4, more preferably at least 6, and preferably up to 12, and more preferably up to 8, carbon atoms), cyclic olefin copolymers (COC's), other olefin copolymers (especially copolymers of ethylene with another olefin monomer, such as a $C_1$ to $C_{12}$ alken-1-yl group) and homopolymers (for example, those made using conventional heterogeneous catalysts), polyphenylene ether polymers (PPO) and any combination or blend thereof.

Thermoplastic polymers are well-known by those skilled in the art, as well as methods for making them.

In one embodiment, the thermoplastic polymer is a rubber-modified monovinylidene aromatic polymer produced by polymerizing a vinyl aromatic monomer in the presence of a dissolved elastomer or rubber. Vinyl aromatic monomers include, but are not limited to those described in U.S. Pat. Nos. 4,666,987; 4,572,819 and 4,585,825. Preferably, the monomer is of the Formula (XXXIII):

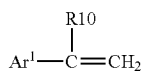

Formula (XXXIII)

wherein "R10" is hydrogen or methyl, "Ar" is an aromatic ring structure having from 1 to 3 aromatic rings with or without alkyl, halo, or haloalkyl substitution, wherein any alkyl group contains 1 to 6 carbon atoms and haloalkyl refers to a halo-substituted alkyl group. Preferably, "$Ar^1$" is phenyl or alkylphenyl, wherein alkylphenyl refers to an alkyl substituted phenyl group, with phenyl being most preferred. Typical vinyl aromatic monomers which can be used include, for example, styrene, alpha-methylstyrene, all isomers of vinyl toluene, especially paravinyltoluene, all isomers of ethyl styrene, propyl styrene, vinyl biphenyl, vinyl naphthalene, vinyl anthracene, and mixtures thereof. The vinyl aromatic monomers may also be combined with other copolymerizable monomers. Examples of such monomers include, but are not limited to acrylic monomers such as acrylonitrile, methacrylonitrile, methacrylic acid, methyl methacrylate, acrylic acid, and methyl acrylate; maleimide, phenylmaleimide, and maleic anhydride, and mixtures thereof.

The rubber used to produce the rubber modified monovinylidene aromatic polymer can be any rubber which will enhance the impact properties of the monovinylidene aromatic polymer, including any molecular architecture such as linear, branched, star branched, and homo- and copolymer diene rubbers, block rubbers, functionalized rubbers, low cis, high cis rubbers and mixtures thereof. The elastomer or rubber preferably employed are those polymers and copolymers which exhibit a second order transition temperature which is not higher than 0° C., preferably not higher than 20° C., and more preferably not higher than 40° C. as determined or approximated using conventional techniques, for example, ASTM test method D 52 T.

The rubber is typically used in amounts such that the rubber-reinforced polymer product contains from 3, preferably from 4, more preferably from 5 and most preferably from 6 to 20, preferably to 18 percent, more preferably to 16 and most preferably to 14 weight percent rubber, based on the total weight of the vinyl aromatic monomer and rubber components, expressed as rubber or rubber equivalent. The term "rubber" or "rubber equivalent," as used herein, is intended to mean, for a rubber homopolymer, such as polybutadiene, simply the amount of rubber, and for a block copolymer, the amount of the copolymer made up from monomer which when homopolymerized forms a rubbery polymer, such as for a butadiene-styrene block copolymer, the amount of the butadiene component of the block copolymer.

The rubber is present as discrete rubber particles within the monovinylidene aromatic polymer matrix, and can have any type, including monomodal, bimodal or multimodal particle size distribution and particle size, as well as any morphology including cellular, core shell, onion-skin, as well as any combinations thereof.

Polymerization processes and process conditions for the polymerization of vinyl aromatic monomers, production of rubber modified polymers thereof and the conditions needed for producing the desired average particle sizes, are well known to one skilled in the art. Although any polymerization process can be used, typical processes are continuous bulk or solution polymerizations as described in U.S. Pat. Nos. 2,727,884 and 3,639,372. The polymerization of the vinyl aromatic monomer is conducted in the presence of predissolved elastomer to prepare impact modified, or grafted rubber containing products, examples of which are described in U.S. Pat. Nos. 3,123,655; 3,346,520; 3,639,522; and 4,409,369, which are incorporated by herein reference. The rubber is typically a butadiene or isoprene rubber, preferably polybutadiene. Preferably, the rubber modified vinyl aromatic polymer is high impact polystyrene (HIPS) or acrylonitrile-butadiene-styrene (ABS), with HIPS being most preferred.

The thermoplastic polymer or polymer blend is employed in the halogen-free ignition resistant polymer compositions of the present invention in amounts of at least 35 parts by weight, preferably at least 40 parts by weight, more preferably at least 45 parts by weight, and most preferably at least 50 parts by weight based on 100 parts by weight of the halogen-free ignition resistant polymer composition of the present invention. In general, the thermoplastic polymer component is employed in amounts less than or equal to 99 parts by weight, preferably less than or equal to 95 parts by weight, more preferably less than or equal to about 90 parts by weight, and most preferably less than or equal to about 85 parts by weight based on 100 parts by weight of the halogen-free ignition resistant polymer composition of the present invention.

In one embodiment, the halogen-free ignition resistant polymer composition of the present invention comprises Compound (I) with a blend of two thermoplastic polymers wherein at least one of the thermoplastic polymers is for example a polyphenylene ether. Polyphenylene ethers are made by a variety of well known catalytic and non-catalytic processes from corresponding phenols or reactive derivatives thereof. By way of illustration, certain of the polyphenylene ethers useful in the present invention are disclosed in U.S. Pat. Nos. 3,306,874; 3,306,875, 3,257,357 and 3,257,358.

The polyphenylene ether resins are preferably of the type having the repeating structural Formula (XXXIV):

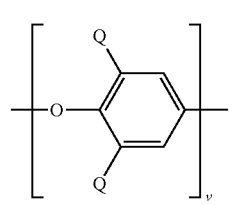

Formula (XXXIV)

wherein the oxygen ether atom of one unit is connected to the benzene nucleus of the next adjoining unit, "v" is a positive integer and is at least 50 and preferably up to about 100,000, and each "Q" is a mono-valent substituent selected from the group consisting of hydrogen, halogen, hydrocarbon radicals free of a tertiary alpha carbon atom, halohydrocarbon radicals having at least two carbon atoms between the halogen atom and the phenyl nucleus, hydrocarbonoxy radicals and halohydrocarbonoxy radicals having at least two carbon atoms. The preferred polyphenylene ether resin is poly(2,6-dimethyl-1,4-phenylene)ether resin.

When used in combination with another thermoplastic polymer, the polyphenylene ether resin is preferably employed in the halogen-free ignition resistant polymer compositions of the present invention in amounts of at least 5 parts by weight, preferably 10 part by weight, more preferably at least 12 parts by weight, more preferably at least 15 parts by weight, and most preferably at least 18 parts by weight to 30 parts by weight, preferably to 28 parts by weight, more preferably to 25 parts by weight, based on 100 parts by weight of the halogen-free ignition resistant polymer composition of the present invention. The thermoplastic and polyphenylene ether polymer can be prepared as a blend prior to incorporation into the composition of the present invention, or each polymer can be incorporated individually.

In one embodiment of the present invention, the ignition resistant thermoplastic polymer composition according to the present invention may optionally contain an epoxidized Compound (I), a benzoxazine ring-containing compound or a thermolabile group-containing compound according to the present invention as described above.

In another alternative embodiment of the present invention, the ignition resistant thermoplastic polymer composition of the present invention may be a blend of (i) one or more thermoplastic resins and (ii) an epoxidized Compound (I), a benzoxazine-ring containing compound or a thermolabile group-containing compound according to the present invention as described above.

The composition of the present invention may include other additives such as modifiers that include compounds containing functionalities which will enhance the mechanical properties of the composition and are compatible with the thermoplastic resin. For thermoplastic resins such as monovinylidene aromatics and conjugated dienes, such functionalities might include, but are not limited to, butadienes, styrene-maleic anhydrides, polybutadiene-maleic anhydride copolymers, carboxylic acid terminated butadienes, and carboxylic acid functionalized polystyrenes. Any combination of modifiers can be used in modifying the phosphorus element-containing epoxy compounds.

The amount of Compound (I), epoxidized Compound (I), benzoxazine-ring containing compound, or thermolabile group-containing compound used in the ignition resistant thermoplastic polymer composition of the present invention is typically at least 1 weight-percent, generally at least 5 weight-percent, preferably at least 10, more preferably at least 15, and most preferably at least 20, weight-percent and less than 50, preferably less than 45, more preferably less than 40 and most preferably less than 35, weight-percent, based on the total weight of the ignition resistant polymer composition.

Preparation of the ignition resistant polymer composition of the present invention can be accomplished by any suitable mixing means known in the art, including dry blending the individual components and subsequently melt mixing, either directly in the extruder used to make the finished article or pre-mixing in a separate extruder. Dry blends of the compositions can also be directly injection molded without pre-melt mixing.

When softened or melted by the application of heat, the ignition resistant thermoplastic polymer composition of this invention can be formed or molded using conventional techniques such as compression molding, injection molding, gas assisted injection molding, calendaring, vacuum forming, thermoforming, extrusion and/or blow molding, alone or in combination. The ignition resistant thermoplastic polymer composition can also be formed, spun, or drawn into films, fibers, multi-layer laminates or extruded sheets, or can be compounded with one or more organic or inorganic substances, on any machine suitable for such purpose.

In one embodiment, the composition of the present invention can be utilized in the preparation of a foam. The ignition resistant polymer composition is extruded into foam by melt processing it with a blowing agent to form a foamable mixture, extruding said foamable mixture through an extrusion die to a region of reduced pressure and allowing the foamable mixture to expand and cool. Conventional foam extrusion equipment, such as screw extruders, twin screw extruders and accumulating extrusion apparatus can be used. Suitable processes for making extruded foams from resin/blowing agent mixtures are described in U.S. Pat. Nos. 2,409,910; 2,515,250; 2,669,751; 2,848,428; 2,928,130; 3,121,130; 3,121,911; 3,770,688; 3,815,674; 3,960,792; 3,966,381; 4,085,073; 4,146,563; 4,229,396; 4,302,910; 4,421,866; 4,438,224; 4,454,086 and 4,486,550.

In another embodiment of the present invention, the halogen-free ignition resistant polymer composition of the present invention may optionally include, in addition to Compound (I), other phosphorus-containing compounds. Optionally, the composition of the present invention may also include other flame retardant additives which can be phosphorus or non-phosphorus materials as described above.

The amount of optional phosphorus-containing compounds, other than Compound (I), and/or the optional flame retardant additives used in the composition of the present invention may be from 0 up to 30 weight percent. The amount of optional phosphorus-containing component, other than Compound (I), when present, is preferably at least 1 weight-percent and preferably up to 30 weight-percent based on the total weight of the thermoplastic resin.

The amount of component, Compound (I), is preferably at least 5 weight-percent and preferably up to 20 weight-percent, based on the total weight of the thermoplastic resin.

The ignition resistant thermoplastic resin is preferably substantially free of bromine atoms, and more preferably substantially free of halogen atoms, as the expression "substantially free" is defined above.

The halogen-free ignition resistant polymer compositions of the present invention are useful to fabricate numerous useful articles and parts. Some of the articles which are particularly well suited include television cabinets, computer monitors, related printer housings which typically requires to have excellent flammability ratings. Other applications include automotive and small appliances.

Ignition-Resistant Thermosetting Composition

In another embodiment of the present invention, the phosphorus-containing product, Compound (I), obtainable by reacting Component (A) with Component (B) is used to make phosphorus-containing ignition resistant thermosetting composition.

A halogen-free ignition-resistant thermosetting composition is obtainable by blending (i) the phosphorus-containing compound, Compound (I), according to the present invention with (ii) at least one thermosetting system. Examples of thermosetting systems are epoxy, polyurethane, polyisocyanates, benzoxazine ring-containing compounds, unsaturated resin systems containing double or triple bonds, polycyanate ester, bismaleimide, triazine, bismaleimide and mixtures thereof.

In another embodiment of the present invention, the ignition resistant thermosetting polymer composition according to the present invention may optionally contain an epoxidized Compound (I), a benzoxazine ring-containing compound or a thermolabile group-containing compound according to the present invention as described above.

In another alternative embodiment of the present invention, the ignition resistant thermosetting polymer composition of the present invention may be a blend of (i) one or more thermosetting systems and (ii) an epoxidized Compound (I), a benzoxazine ring containing compound or a thermolabile group containing compound according to the present invention as described above.

Ignition-Resistant Thermoplastic/Thermosetting Hybrid Systems

In another embodiment of the present invention, the phosphorus-containing product, Compound (I), obtainable by reacting Component (A) with Component (B) is used to make phosphorus-containing ignition resistant hybrid resin system that contains both a thermoplastic and a thermosetting system.

The hybrid ignition-resistant thermoplastic and thermosetting compositions are obtainable by blending (i) the phosphorus-containing compound, Compound (I), according to the present invention with (ii) a thermoplastic resin and (iii) a thermosetting system. Examples of thermoplastic resins are polyphenylene oxide (PPO), mixtures thereof, and others as described in the above paragraph. Examples of thermosetting systems are epoxy, polyurethane, polyisocyanates, benzoxazine ring-containing compounds, unsaturated resin systems containing double or triple bonds, polycyanate ester, bismaleimide, triazine, bismaleimide and mixtures thereof.

In another embodiment of the present invention, the ignition resistant thermoplastic/thermosetting hybrid polymer composition according to the present invention may optionally contain an epoxidized Compound (I), a benzoxazine ring-containing compound or a thermolabile group-containing compound according to the present invention as described above.

In another alternative embodiment of the present invention, the ignition resistant thermoplastic/thermosetting hybrid polymer composition of the present invention may be a blend of (i) one or more thermoplastic resins, (ii) one or more thermosetting systems and (iii) an epoxidized Compound (I), a benzoxazine ring-containing compound or a thermolabile group-containing compound according to the present invention as described above.

The compositions described above are useful for making coating formulations, encapsulation, composites, adhesives, molding, bonding sheets, laminated plates. As an illustration, a coating formulation may comprise (i) Compound (I), (ii) a solid epoxy resin, and (iii) a hardener such as an amine or phenolic hardener.

The following examples illustrate how one may practice the present invention. Those who are skilled in this field of technology are capable of practicing the full scope of the present invention via procedures analogous to those described below.

EXAMPLES

The materials used in the examples are described below:

The test procedures used to measure the properties of the various materials of the examples are further described below:

| Property Measured | Measurement Procedure |
| --- | --- |
| TMA | Thermo-mechanical analysis via IPC-TM-650-#2.4.24C |
| T-288 | Time to delamination at 288° C. measured by TMA via method IPC-TM-650-#2.4.24:1 |
| Tg | Glass transition temperature measured in degrees Celsius according to IPC-TM-650-2.4.25 |
| UL 94 Flammability | Flammability test according to IPC-TM-650-2.3.10 |
| CTE<Tg/>Tg | Coefficient of thermal expansion below Tg and after Tg |
| HPCT | High pressure cooker test reporting weight percent water pick-up & percent passed solder bath @ 260 C. according to IPC-TM-650-2.6.16 |
| Cu peel, N/cm | Copper peel strength measured using the method described in IPC-TM-650-#2.4.8C |
| $V_O$ rating | Rating used in the UL 94 Flammability test. |

The IPC test methods are the electrical laminate industry standards developed by The Institute For Interconnection And Packaging Electronic Circuits, 3451 Church Street, Evanston, Ill. 60203.

Preparation of phosphorus-containing compounds according to the present invention is illustrated by the following examples.

| Designation | Description |
| --- | --- |
| Struktol Polydis ™ PD 3710 | 3,4,5,6-dibenzo-1,2-oxaphosphane-2-oxide, available from Schill & Seilacher GmbH & Co., a company incorporated in Germany |
| SANTOLINK EP 560 | Butyl etherified phenol and formaldehyde condensation product, available from UCB Group, a company headquartered in Brussels, Belgium, and its affiliate, UCB GmbH & Co. KG, a company incorporated in Germany |
| PHENODUR VPR 1785/50 | Butyl etherified phenol and formaldehyde condensation product with a weight average molecular weight from 4000 to 6000 and a polydispersity from 2 to 3, available from UCB Group, a company headquartered in Brussels, Belgium, and its affiliate, UCB GmbH & Co. KG, a company incorporated in Germany |
| PHENODUR PR 411 | Butyl etherified bisphenol A and formaldehyde condensation product, available from UCB Group, a company headquartered in Brussels, Belgium, and its affiliate, UCB GmbH & Co. KG, a company incorporated in Germany |
| D.E.N. 438 | Liquid epoxy novolac resin having an epoxide equivalent weight of about 180, available from The Dow Chemical Company, a U.S. corporation. |
| DICY | Dicyandiamide |
| Phenol novolac resin | Condensation products obtained from phenol and formaldehyde having a softening point of 95-100° C. and 6-7 hydroxyl group functionality |
| SMA | Styrene maleic anhydride having 20 weight-percent percent maleic anhydride content |
| MEK | Methyl ethyl ketone (an organic solvent) |
| DMF | Dimethyl formamide (a reactive solvent) |
| DOWANOL PMA | Methoxypropylacetate, available from The Dow Chemical Company. |
| Glass cloth reinforcement Type 7628 | Glass cloth reinforcement, available from Porcher Textile, Badinieres, Bourgoin-Jallieu, France |
| Amino silane finish 731 | A glass sizing, available from Porcher Textile, Badinieres, Bourgoin-Jallieu, France |

Example 1

Preparation A 24.69 Grams (gm) of SANTOLINK EP 560 was mixed with 30 gm of Struktol Polydis™ PD 3710 at 170° C. for 10 minutes and heated to 190° C. in 5 minutes and the mixture was held at 190° C. for 20 minutes. The resulting reaction product was placed in a vacuum oven for an additional 30 minutes at 160° C. to complete the reaction by driving out butanol. The weight of the resultant final solid was about 45.6 grams.

The resultant product had a melt viscosity @ 150° C. of 16 Pa·s, and a Tg equal to 78° C. The theoretical phosphorus content of the product was about 9.21 weight percent.

Example 2

Preparation B 480 gm of solid Struktol Polydis™ PD 3710 and 640 gm of Phenodur VPR 1785 (50 percent solid in methoxy propanol) were charged in a 1-liter glass reactor equipped with a mechanical stirrer and a heating jacket, and fitted with a nitrogen gas inlet, a condenser and a solvent collector. The mixture was heated to 120° C. under nitrogen atmosphere to obtain a homogeneous mixture. The homogeneous reaction mixture was heated 1 degree Celsius per minute from 120° C. to 205° C. The solvent (from VPR 1785) and butanol were collected stepwise when the temperature was raised. The reaction mixture was held at 205° C. for 30 minutes until no further volatiles were released from the reaction mixture. The resultant solid material was taken out from the reactor. The total weight of the solid material was 757.8 grams, its Tg was 88° C., and its theoretical phosphorus content was about 8.87 weight percent.

Examples 3-5

The formulations in the table below were prepared with the product of Preparation A described in Example 1 above.

Curable Formulations Based on Preparation A

| Component | Example 3 (Formulation 1) | Example 4 (Formulation 2) | Example 5 (Formulation 3) |
|---|---|---|---|
| D.E.N. 438 (85 weight. percent in MEK) (parts by weight based on solids) | 67 | 30 | 55 |
| Product of Preparation A (60 wt. percent in MEK) (parts by weight based on solids) | 33 | 35 | 27 |
| DICY (20 wt. percent in DMF) (parts by weight based on solids) | 2 | 0 | 0 |
| Phenol novolac (50 wt. percent in DOWANOL PMA) (parts by weight based on solids) | 0 | 0 | 18 |
| SMA (parts by weight based on solids) | 0 | 35 | 0 |
| Boric acid (20 wt. percent in methanol) (parts by weight based on solids) | 0.6 | 0.6 | 0.6 |
| 2-phenylimidazole (20 wt. percent in DOWANOL PMA) (parts by weight based on solids) | 1.5 | 0 | 0.6 |
| 2-ethyl, 4-methyl imidazole (20 wt. percent in DOWANOL PMA) (parts by weight based on solids) | 0 | 0.2 | 0 |
| Properties | | | |
| Gel time at 170° Celsius in seconds | 182 | 264 | 220 |
| Glass transition temperature (Tg) in degrees Celsius | 170 | 166 | 171 |

For each Formulation 1, 2, and 3, the above components were combined and mixed at room temperature (~25° C.) for about 60 minutes to form a varnish suitable for the measurement of gel time and glass transition temperature of the cured products.

Example 6

Formulation 1 described in Example 3 above was impregnated into a glass cloth reinforcement substrate having amino silane finish 731. The impregnated substrate is passed through a CARATSCH pilot treater (built by Caratsch AG, Bremgarten, Switzerland) having a 3 meter horizontal oven at an air temperature of approximately 177° C. and a winding speed of 1.4 meters per minute to form a prepreg. The resulting prepreg had a resin content of about 34.5 wt. percent and a residual gel time of 145 seconds at 171° C.

The prepreg formed above was cut into eight samples (30 cm×30 cm samples) and then a laminate was formed from the prepreg samples as follows: eight layers of prepregs together with two layers of copper were pressed together at 190° C. for 90 minutes to obtain a laminate having a TMA thickness of about 1.48 mm The laminate had a TMA Tg of about 163° C., a CTE<Tg/>Tg of 40.2/241.9, and a T-288 greater than 60 minutes. The copper peel strength of the laminate was about 14.3 N/cm. The laminate passed the UL 94 Flammability Vo rating.

Example 7

Preparation C 440 gm of solid Struktol Polydis™ PD 3710 and 720 gm of Phenodur VPR 1785 (50 percent solid in methoxy propanol) were charged in a 1-liter glass reactor equipped with a mechanical stirrer and a heating jacket, and fitted with a nitrogen gas inlet, a condenser and a solvent collector. The mixture was heated from 100 degree Celsius to 201° C. in 155 min The solvent (from VPR 1785) and butanol were collected stepwise when the temperature was raised. The reaction mixture was held at 201° C. for 40 minutes until no further volatiles were released from the reaction mixture. The resultant solid material was taken out from the reactor. The Tg was 104° C., and the melt viscosity at 200° C. is 2.34 Pas.

The resulting product of this example is believed to be a blend of oligomers wherein one of the oligomers has the following structure:

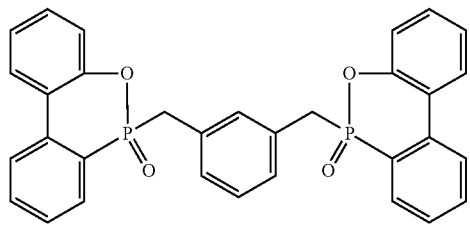

Example 8

Preparation D 558.3 gm of solid Struktol Polydis™ PD 3710 and 391.6 gm of Phenodur PR 411 (75 percent solid in butanol) were charged in a 1-liter glass reactor equipped with a mechanical stirrer and a heating jacket, and fitted with a nitrogen gas inlet, a condenser and a solvent collector. The mixture was heated from 96 degree Celsius to 199° C. in 180 min Butanol were collected stepwise when the temperature was raised. The reaction mixture was held at 200° C. for 20 minutes until no further volatiles were released from the reaction mixture. The resultant solid material was taken from the reactor. The Tg measured by DSC was about 108.5° C.

The resulting product of this example is believed to be a blend of oligomers wherein one of the oligomers has the following structure:

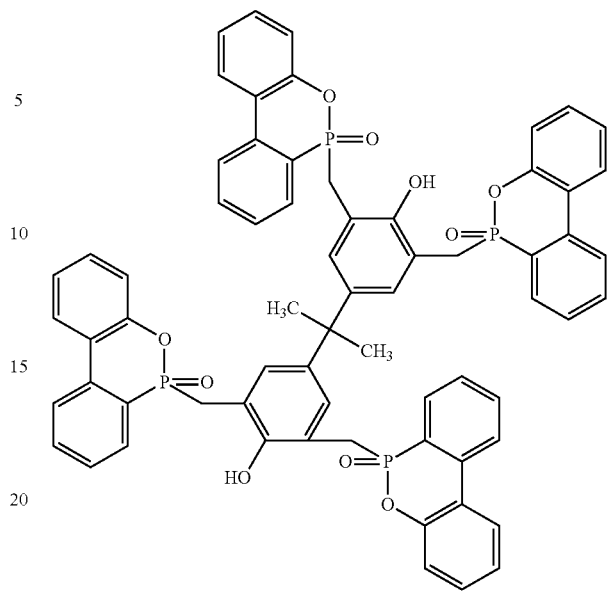

Example 9

Preparation E 405.5 gm of solid Struktol Polydis™ PD 3710 and 391.6 gm of Phenodur PR 411 (75 percent solid in butanol) were charged in a 1-liter glass reactor equipped with a mechanical stirrer and a heating jacket, and fitted with a nitrogen gas inlet, a condenser and a solvent collector. The mixture was heated from 106 degree Celsius to 155° C. in 95 min Butanol were collected stepwise when the temperature was raised. The reaction mixture was held at 155° C. for 300 minutes until no further volatiles were released from the reaction mixture. The resultant solid material was taken from the reactor. The Tg measured by DSC was about 138° C.

The invention claimed is:

1. A process for making a curable phosphorus-containing composition comprising blending:
   (I) a phosphorus-containing compound comprising the reaction product of:
      (A) at least one organophosphorus compound having a group selected from the group H—P═O, the group P—H and the group P—OH; and
      (B) at least one compound having the following Formula (V):

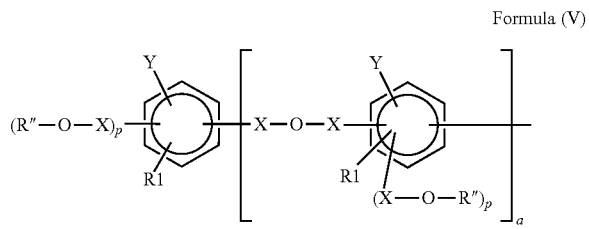

Formula (V)

-continued

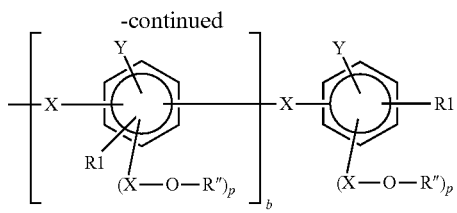

wherein

R1 each independently is hydrogen or an alkyl group having from 1 to 10 carbon atoms;

Y is a functional group selected from hydroxy, carboxylic acid, carboxylate, acid anhydride, and amine;

X is a hydrocarbylene group;

R" is a hydrocarbyl group having from 1 to 8 carbon atoms;

p each independently represents a number from one to 4; and a and b each independently represent a number greater than zero; and (II) a thermosetting composition.

2. The process of claim 1 wherein the thermosetting composition, Component (II), contains an epoxy resin.

3. The process of claim 1 wherein the thermosetting composition, Component (II), contains a polyisocyanate.

4. The process of claim 1 wherein the thermosetting composition, Component (II), contains a polymerizable unsaturated compound.

5. The process of claim 4 wherein the polymerizable unsaturated compounds are selected from the group consisting of vinylesters, acrylates, cyanate esters, and cyanamides.

6. The process of claim 2 wherein the thermosetting composition, Component (II), contains a benzoxazine-containing compound or a polybenzoxazine-containing compound.

7. The process of claim 1 wherein the thermosetting composition, Component (II), contains bismaleimide, triazines, or a blend of bismaleimide and triazine compounds.

8. The process of claim 1 wherein the thermosetting composition, Component (II), contains an epoxy compound and at least one co-curing agent wherein the co-curing agent is a hydroxyl, an acid, an acid anhydride, a phenolic compound, a nitrogen-containing compound, a compound which generates a reactive group at an elevated temperature, or mixture thereof.

9. The process of claim 8 wherein the acid anhydride is a maleic acid anhydride, a phthalic acid anhydride, methylhexahydrophthalic acid anhydride, a styrene-maleic acid anhydride copolymer, or mixtures thereof.

10. A process for making a curable phosphorus-containing composition comprising blending:
(I) a phosphorus-containing compound comprising the reaction product of:
(A) at least one organophosphorus compound having a group selected from the group H—P═O, the group P—H and the group P—OH; and
(B) at least one compound having the following Formula (VI):

Formula (VI)

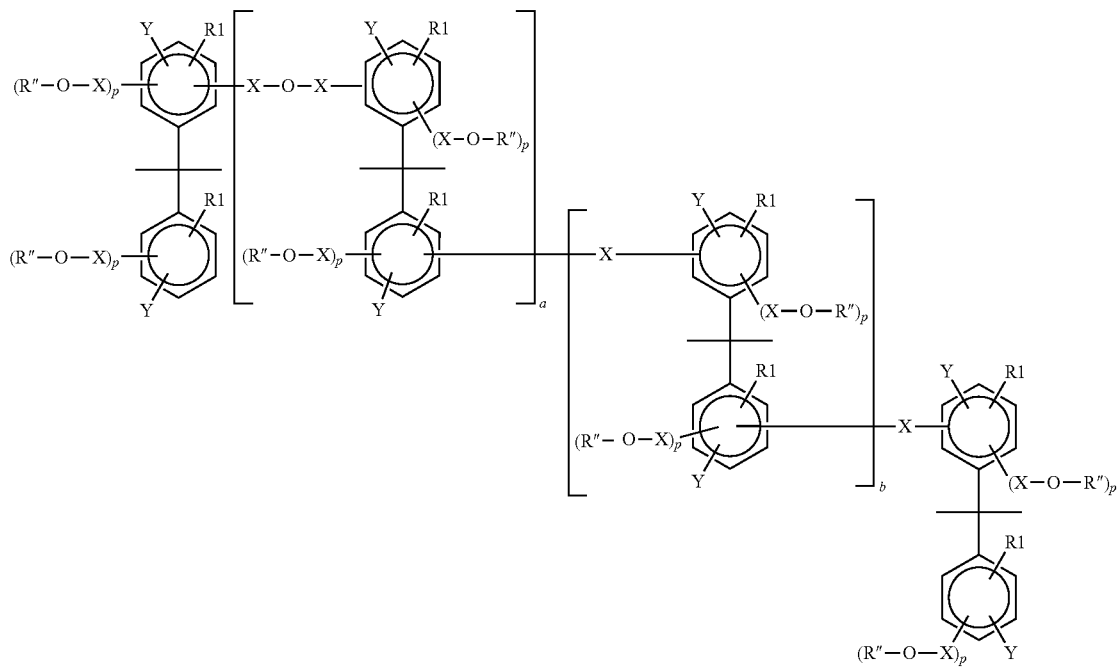

wherein R1 each independently is hydrogen or an alkyl group having from 1 to 10 carbon atoms;

Y is a functional group selected from hydroxy, carboxylic acid, carboxylate, acid anhydride, and amine;

X is a hydrocarbylene group;

R" is a hydrocarbyl group having from 1 to 8 carbon atoms;

p each independently represents a number from zero to 4; and a and b each independently represent a number equal to or greater than zero; and (II) a thermosetting composition.

11. The process of claim 10 wherein the thermosetting composition, Component (II), contains an epoxy resin.

12. The process of claim 10 wherein the thermosetting composition, Component (II), contains an epoxy compound and at least one co-curing agent wherein the co-curing agent is a hydroxyl, an acid, an acid anhydride, a phenolic compound, a nitrogen-containing compound, a compound which generates a reactive group at an elevated temperature, or mixture thereof.

13. The process of claim 12 wherein the acid anhydride is a maleic acid anhydride, a phthalic acid anhydride, methyl-hexahydrophthalic acid anhydride, a styrene-maleic acid anhydride copolymer, or mixtures thereof.

* * * * *